United States Patent [19]
Schaper et al.

[11] Patent Number: 5,821,244
[45] Date of Patent: Oct. 13, 1998

[54] CONDENSED NITROGEN HETEROCYCLES AND THEIR USE AS PESTICIDES, FUNGICIDES AND ANTIMYCOTICS

[75] Inventors: Wolfgang Schaper, Diedorf; Martin Märkl, Frankfurt; Rainer Preuss, Berlin; Robert Klein, Frankfurt; Gerhard Salbeck, deceased, late of Kriftel, by Gisela Salbeck, heiress; Peter Braun, Nieder-Olm; Werner Knauf, Liederbach; Burkhard Sachse, Kelkheim; Anna Waltersdorfer, Frankfurt; Manfred Kern, Lörzweiler; Peter Lümmen, Niedernhausen; Werner Bonin, Kelkheim, all of Germany

[73] Assignee: Hoechst Schering AgrEvo GmbH, Berlin, Germany

[21] Appl. No.: 501,006
[22] PCT Filed: Mar. 4, 1994
[86] PCT No.: PCT/EP94/00643
§ 371 Date: Jan. 11, 1996
§ 102(e) Date: Jan. 11, 1996
[87] PCT Pub. No.: WO94/21613
PCT Pub. Date: Sep. 29, 1994

[30] Foreign Application Priority Data

Mar. 13, 1993 [DE] Germany .............. 43 08 014.6

[51] Int. Cl.$^6$ .............. A61K 31/54; A61K 31/535; C07D 403/02; C07D 403/14
[52] U.S. Cl. .............. 514/248; 514/250; 514/258; 544/279; 544/283; 544/284; 544/287; 544/293; 544/350
[58] Field of Search ............ 544/279, 283, 544/284, 287, 293, 350; 514/250, 258, 248

[56] References Cited

FOREIGN PATENT DOCUMENTS

| 0 326 328 | 8/1989 | European Pat. Off. . |
| 0 326 330 A2 | 8/1989 | European Pat. Off. . |
| 0 326 331 | 8/1989 | European Pat. Off. . |
| 0 410 762 | 1/1991 | European Pat. Off. . |
| 0 414 386 | 2/1991 | European Pat. Off. . |
| WO 93/19050 | 9/1993 | WIPO . |

*Primary Examiner*—Matthew V. Grumbling
*Attorney, Agent, or Firm*—Frommer Lawrence & Haug LLP

[57] ABSTRACT

Condensed nitrogen heterocycles, process for their preparation, and their use as antimycotics The invention relates to compounds of the formula

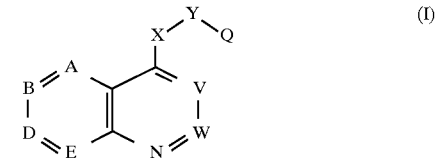

in which two of the symbols A, B, D and E in each case are $CR^1$ and the remaining two symbols are in each case CH or in each case nitrogen or one of the remaining two symbols is CH and the other is nitrogen and one of the symbols V and W is $CR^2$ and the other is CH or nitrogen, $R^1$ and $R^2$ are in each case H, halogen, alkyl, alkoxy, haloalkyl or haloalkoxy, X is optionally substituted imino, S, SO or $SO_2$, Y is a bond or alkanediyl, Q is substituted cycloalkyl or substituted 4-piperidinyl, to processes for the preparation, to compositions containing them, and to their use as pesticides, fungicides and antimycotic agents.

34 Claims, No Drawings

CONDENSED NITROGEN HETEROCYCLES AND THEIR USE AS PESTICIDES, FUNGICIDES AND ANTIMYCOTICS

This application claims priority under 35 U.S.C. § 371 from PCT/EP94/00643, filed Mar. 4, 1994.

It has already been disclosed that certain 4-amino- and 4-alkoxy-substituted quinolines, cinnolines, naphthyridines, pyridopyrimidines and pteridines show a fungicidal, acaricidal and insecticidal activity (cf. EP-A-326 328, EP-A-326 330, EP-A-326 331, EP-A-410 762, EP-A-414 386). However, the biological activity of these compounds is not satisfactory in all fields of application, in particular when low application rates and concentrations are used.

Novel 4-amino- and 4-alkoxy-substituted condensed nitrogen heterocycles of the formulae 1a to 1d

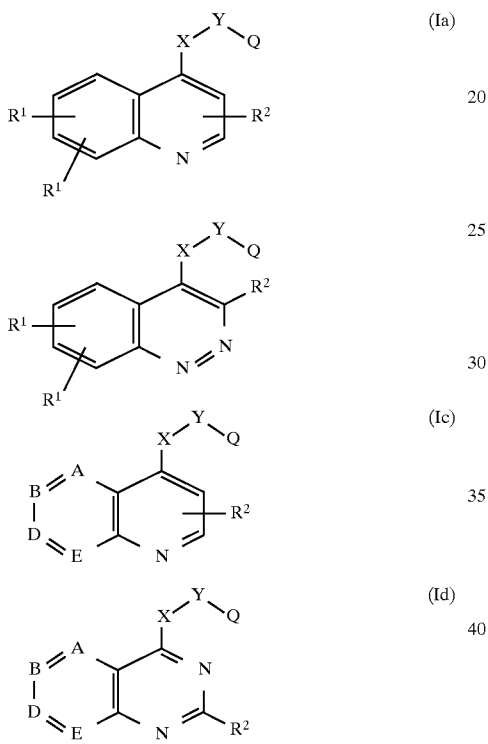

in which the radicals and groups are defined below, which are well tolerated by plants and of favorable toxicity to warm-blooded species while being highly suitable for controlling animal pests, such as insects, arachnids, nematodes, helminths and molluscs, for controlling endo- and ectoparasites in the field of veterinary medicine and for controlling fungal pests, have been found.

The invention therefore relates to compounds of the formula I

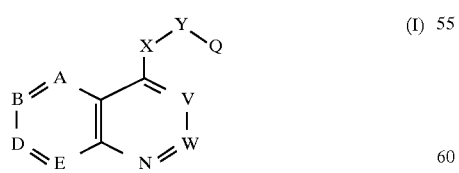

in which two of the symbols A, B, D and E are in each case $CR^1$ and the remaining two symbols are in each case CH or in each case nitrogen, or one of the remaining two symbols is CH and the other is nitrogen, one of the symbols V and W is $CR^2$ and the other is CH or nitrogen, $R^1$ radicals are identical or different and are hydrogen, halogen, $(C_1-C_4)$-alkyl, $(C_1-C_4)$-alkoxy, halo-$(C_1-C_4)$-alkyl or halo-$(C_1-C_4)$-alkoxy, where, preferably, one radical $R^1$ is always hydrogen, $R^2$ is hydrogen, halogen, $(C_1-C_4)$-alkyl, $(C_1-C_4)$-alkoxy, halo-$(C_1-C_4)$-alkyl or halo-$(C_1-C_4)$-alkoxy, X is NR, oxygen, sulfur, SO or $SO_2$, preferably NR or oxygen, R is hydrogen or $(C_1-C_4)$-alkyl, preferably hydrogen, Y is a direct bond or a straight-chain or branched $(C_1-C_4)$-alkanediyl group, Q is $Q^1$ and $Q^1$ is a cycloalkyl group of the formula II

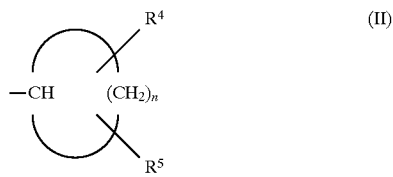

in which n is an integer from 2 to 7, $R^4$ and $R^5$ are identical or different and are in each case hydrogen, $(C_1-C_{12})$-alkyl, $(C_3-C_8)$-cycloalkyl, $(C_3-C_8)$-cycloalkyl-$(C_1-C_4)$-alkyl, $(C_1-C_8)$-alkoxy, $(C_3-C_8)$-cycloalkoxy, $(C_1-C_4)$-alkoxy-$(C_1-C_4)$-alkyl, $(C_3-C_8)$-cycloalkyl-$(C_1-C_4)$-alkoxy, $(C_1-C_8)$-alkoxycarbonyl, $(C_1-C_4)$-alkoxy-$(C_1-C_4)$-alkylcarbonyl, $(C_3-C_8)$-cycloalkoxycarbonyl, $(C_1-C_8)$-alkylcarbamoyl, di-$(C_1-C_8)$-alkylcarbamoyl, N-piperidinocarbonyl, N-morpholino-carbonyl, $(C_3-C_8)$-cycloalkylcarbamoyl, $(C_1-C_8)$-alkylcarbonyloxy, $(C_3-C_8)$-cycloalkylcarbonyloxy, $(C_1-C_8)$-alkylcarbonylamino, $(C_3-C_8)$-cycloalkylcarbonylamino, tri-$(C_1-C_8)$-alkylsilyl, preferably dimethyl-$(C_1-C_8)$-alkylsilyl or triethylsilyl, di-$(C_1-C_8)$-alkyl-$(C_3-C_8)$-cycloalkylsilyl, preferably dimethylcyclohexylsilyl, di-$(C_1-C_8)$-alkyl-(phenyl-$(C_1-C_4)$-alkyl)silyl, preferably dimethyl-(phenyl-$(C_1-C_4)$-alkyl-silyl, di-$(C_1-C_8)$-alkyl-$(C_1-C_4)$-haloalkylsilyl, preferably dimethyl-$(C_1-C_4)$-haloalkylsilyl, dimethylphenylsilyl, $(C_1-C_4)$-haloalkyl, halogen, $(C_1-C_4)$-haloalkoxy, $(C_1-C_4)$-haloalkoxycarbonyl, $(C_1-C_4)$-haloalkylcarbamoyl, $(C_3-C_8)$-haloalkylcarbonyloxy, $(C_3-C_8)$-haloalkylcarbonylamino, heteroaryl, phenyl, naphthyl, biphenylyl, phenyl-$(C_1-C_4)$-alkyl, benzyloxy, benzyloxy-$(C_1-C_4)$-alkyl, benzylthio, phenoxycarbonyl, benzyloxycarbonyl, phenylcarbamoyl, benzylcarbamoyl, benzoyloxy, phenylacetyloxy, benzoylamino, phenylacetylamino, phenylthio or phenoxy, it being possible for the phenyl rings in the 17 last-mentioned radicals and in heteroaryl to be unsubstituted or provided with one or two substituents, and these substituents are identical or different and can in each case be $(C_1-C_8)$-alkyl, $(C_3-C_8)$-cycloalkyl, $(C_1-C_4)$-haloalkyl, preferably trifluoromethyl, halogen, $(C_1-C_4)$-dialkylamino, $(C_1-C_4)$-alkylthio, $(C_1-C_8)$-alkoxy, $(C_1-C_4)$-haloalkoxy, $(C_1-C_4)$-alkoxy-$(C_1-C_4)$-alkoxy, $H_5C_2$—O—$[CH_2$—$CH_2$—O—$]_x$ where x=2, 3 or 4, 2-(tetrahydro-2H-pyran-2-yloxy)-ethoxy, $(C_2-C_8)$-alkenyl, $(C_2-C_8)$-alkynyl, benzyloxy, which optionally has one or two identical or different substituents from the series comprising $(C_1–C_4)$-alkyl, $(C_1–C_4)$-haloalkyl, $(C_1–C_4)$-alkoxy, $(C_1–C_4)$-haloalkoxy and halogen in the phenyl radical, or tri-$(C_1–C_4)$-alkylsilylmethoxy, preferably dimethyl-$(C_1–C_4)$-alkylsilylmethoxy, $(C_3–C_8)$-cycloalkyl-$(C_1–C_4)$alkoxy, 1,3-dioxolan-2-ylmethoxy, tetrahydrofur-2-ylmethoxy or tetrahydro-2H-pyran-2-ylmethoxy, it being possible for in each case one hydrogen atom in two adjacent substituents $R^4$ and $R^5{}_1$, which are identical or different and selected from among $(C_1–C_8)$-alkyl and $(C_1–C_8)$-alkoxy, to be replaced by a joint C—C bond which links these two substituents, with the proviso that $R^4$ and $R^5$ cannot simultaneously both be hydrogen, and that, in the event that one of the radicals $R^4$ and $R^5$ is hydrogen, the other cannot be methyl, and that, in the event that A, B, D, V and W are in each case CH, E is CF, X is O and Y is a bond, then Q is not 2-phenylcyclohexyl, or $R^4$ and $R^5$, if not already embraced by the above definitions, together are $(C_1–C_6)$alkanediyl which is bonded to identical or different carbon atoms, preferably $R^4$ and $R^5$ together with the adjacent carbon atoms to which they are attached form a fused 5- or 6-membered, preferably saturated, isocycle, in particular a cyclopentane or cyclohexane system, in which one or two $CH_2$ groups can be replaced by oxygen or sulfur and one or two ethanediyl groups can be replaced by ethenediyl groups, or Q is $Q^2$ and $Q^2$ is a group of the formula III

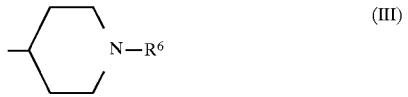

(III)

in which $R^6$ is a group of the formula Z-W and Z is a direct linkage or carbonyl or sulfonyl, and W is an aryl or heteroaryl group which can be unsubstituted or provided with one or two substituents, and these substituents are identical or different and are in each case $(C_1–C_8)$-alkyl, $(C_3–C_8)$-cycloalkyl, trifluoromethyl, halogen, $(C_1–C_4)$-alkoxy, $(C_1–C_4)$-haloalkoxy, $(C_1–C_4)$-dialkylamino or $(C_1–C_4)$-alkylthio.

The present invention relates to the compounds of the formula I in the form of the free base or of a salt, preferably of an acid addition salt. Acids which can be used for salt formation are inorganic acids, such as hydrochloric acid, hydrobromic acid, nitric acid, sulfuric acid and phosphoric acid, or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula I have one or more asymmetric carbon atoms. Racemates and diastereomers can therefore occur. The invention embraces the pure isomers as well as their mixtures. The diastereomer mixtures can be separated into the components by customary methods, for example by selective crystallization from suitable solvents or by chromatography. Racemates can be resolved by customary methods to give the enantiomers, for example by salt formation with an optically active acid, separation of the diastereomeric salts and liberation of the pure enantiomers by means of a base.

If $Q^1$ is a cycloalkyl group of the formula II, then the radicals $R^4$ and $R^5$, unless they are hydrogen, can be in the cis or trans configuration relative to Y. Preferably, at least one of these radicals $R^4$ and $R^5$ is in the cis configuration relative to Y. In particular in the preferred case in which $R^5$ is hydrogen, $R^4$ is preferably in the cis configuration relative to Y, and $R^4$ can be as defined above and also methyl and, if n is 5, 2-phenyl. In the abovementioned radicals of the formula II which are in the cis configuration, $R^4$ preferably is in the $(n+1)/2+1$ position if n is an odd number and in the $n/2+1$ position if n is an even number. In the case of these compounds of the formula I which have the cis configuration, particularly preferred are those in which, in formula II, n is 5 (cyclohexyl) and $R^4$ is in the 4-position.

In the above formula I, "halogen" is to be understood as meaning a fluorine, chlorine, bromine or iodine atom, preferably a fluorine, chlorine or bromine atom;

the term "$(C_1–C_4)$-alkyl" is to be understood as meaning an unbranched or branched hydrocarbon radical having 1 to 4 carbon atoms, such as, for example, the methyl, ethyl, propyl, 1-methylethyl, 2-methylpropyl or 1,1-dimethylethyl radical;

the term "$(C_1–C_8)$-alkyl" is to be understood as meaning the abovementioned alkyl radicals and, for example, the pentyl, 2-methylbutyl, 1,1-dimethylpropyl, hexyl, heptyl, octyl or the 1,1,3,3-tetramethylbutyl radical;

the term "$(C_1–C_{12})$-alkyl" is to be understood as meaning the abovementioned alkyl radicals and, for example, the nonyl, isononyl, decyl, undecyl or the dodecyl radical;

the term "$(C_3–C_8)$-cycloalkyl" is to be understood as meaning the cyclopropyl, cyclobutyl, cyclopentyl, cyclohexyl, cycloheptyl or cyclooctyl group;

the term "$(C_3–C_8)$-cycloalkyl-$(C_1–C_4)$-alkyl" is to be understood as meaning a hydrocarbon radical which is as defined above under the term "$(C_1–C_4)$-alkyl" and which is substituted by one of the hydrocarbon radicals mentioned above under the definition "$(C_3–C_8)$-cycloalkyl", such as, for example, the cyclohexylmethyl, 2-cyclohexylethyl or the 2-cyclohexyl-2-propyl radical;

the term "$(C_1–C_8)$-alkoxy" is to be understood as meaning an alkoxy group whose hydrocarbon radical is as defined under the term "$(C_1–C_8)$-alkyl";

the term "$(C_1–C_4)$-alkoxy-$(C_1–C_4)$-alkyl" is to be understood as meaning, for example, a 1-methoxyethyl group, a 2-methoxyethyl group, a 2-ethoxyethyl group, a methoxymethyl or ethoxymethyl group, a 3-methoxypropyl group or a 4-butoxybutyl group;

the term "$(C_1–C_4)$-haloalkyl" is to be understood as meaning an alkyl group mentioned under the term "$(C_1–C_4)$-alkyl" in which one or more hydrogen atoms is replaced by the abovementioned halogen atoms, preferably chlorine or fluorine, such as, for example, the trifluoromethyl group, the 2,2,2-trifluoroethyl group, the chloromethyl or fluoromethyl group, the difluoromethyl or 1,1,2,2-tetrafluoroethyl group;

the term "$(C_1–C_4)$-haloalkoxy" is to be understood as meaning a haloalkoxy group whose halohydrocarbon radical is as defined under the term "$(C_1–C_4)$-haloalkyl";

the term "phenyl-$(C_1–C_4)$-alkyl" is to be understood as meaning one of the abovementioned $(C_1–C_4)$-alkyl groups which is substituted by a phenyl group, for example the benzyl, 2-phenylethyl, 1-phenylethyl, 1-methyl-1-phenylethyl group, the 3-phenylpropyl or the 4-phenylbutyl group, the term "di-$(C_1–C_4)$-alkylamino" is to be understood as meaning a dialkylamino group whose hydrocarbon radicals are as defined under the term "($C_1$–$C_4$)-alkyl", preferably the dimethylamino and diethylamino group, the term "aryl" is preferably to be understood as meaning ($C_6$–$C_{12}$)-aryl, such as, for example, phenyl, naphthyl or biphenylyl, in particular phenyl;

the term "heteroaryl" is to be understood as meaning an aryl radical as defined above in which at least one CH group is replaced by N and/or at least two adjacent CH groups are replaced by S, NH or O, examples of such radicals being thienyl, furyl, benzofuryl, pyrrolyl, imidazolyl, pyrazolyl, pyridyl, pyrazinyl, pyrimidinyl, pyridazinyl, oxazolyl, isoxazolyl, thiazolyl, isothiazolyl and tetrazolyl;

the term "($C_3$–$C_8$)-cycloalkoxy" is to be understood as meaning a cycloalkoxy group whose hydrocarbon radical is as defined under "($C_3$–$C_8$)-cycloalkyl";

the term "($C_1$–$C_4$)-alkylthio" is to be understood as meaning an alkylthio group whose hydrocarbon radical is as defined under the term "($C_1$–$C_4$)-alkyl";

the term "($C_1$–$C_4$)-alkylthio-($C_1$–$C_4$)-alkyl" is to be understood as meaning, for example, methylthiomethyl, ethylthiomethyl, propylthiomethyl, 2-methylthioethyl, 2-ethylthioethyl or 3-methylthiopropyl;

the term "benzyloxy-($C_1$–$C_4$)-alkyl" is to be understood as meaning a ($C_1$–$C_4$)-alkyl group as defined above which is substituted by a benzyloxy group, for example the benzyloxymethyl or the 2-(benzyloxy)ethyl group;

the term "($C_3$–$C_8$)-cycloalkyl-($C_1$–$C_4$)-alkoxy" is to be understood as meaning a ($C_1$–$C_4$)-alkoxy group as defined above which is substituted by a ($C_3$–$C_8$)-cycloalkyl group as defined above, for example the cyclopropylmethyloxy or the cyclohexylmethyloxy group;

the term "tri-($C_1$–$C_8$)-alkylsilyl" is to be understood as meaning a trialkylsilyl group having preferably two methyl groups and one ($C_1$–$C_8$)-alkyl group as defined above, for example the trimethylsilyl, the dimethylethylsilyl or the dimethyloctylsilyl group;

the term "di-($C_1$–$C_8$)-alkyl-($C_1$–$C_4$)-haloalkylsilyl" is to be understood as meaning a silyl radical having preferably two methyl groups and one ($C_1$–$C_4$)-haloalkyl radical as defined under the term ($C_1$–$C_4$)-haloalkyl, for example the dimethyl-3,3,3-trifluoropropylsilyl radical;

the term "($C_1$–$C_4$)-alkoxy-($C_1$–$C_4$)-alkoxyl" is to be understood as meaning, for example, the methoxymethyl, ethoxymethoxy, 2-ethoxyethoxy, 2-butoxyethoxy or 2-methoxyethoxy group;

the term "($C_2$–$C_8$)-alkenyl" is to be understood as meaning, for example, the allyl, 1-methylallyl, 2-butenyl or 3-methyl-2-butenyl group;

the term "($C_2$–$C_8$)-alkynyl" is to be understood as meaning, for example, the propargyl, 2-butynyl or 2-pentynyl group;

the term "tri-($C_1$–$C_4$)-alkylsilylmethoxyl" is to be understood as meaning a trialkylsilylmethoxy radical having preferably 2 methyl groups in which the ($C_1$–$C_4$)-alkyl group is as defined above;

the term "di-($C_1$–$C_8$)-alkylphenyl-($C_1$–$C_4$)-alkylsilyl is to be understood as meaning a trialkylsilyl radical having preferably two methyl groups, in which one alkyl group is as defined above for the term "phenyl-($C_1$–$C_4$)-alkyl", preferably the dimethylbenzylsilyl group.

If $R^4$ and $R^5$ represent ($C_1$–$C_6$)-alkanediyl, they are preferably either on the same carbon atom, with which they form a spirocyclic ring system, or on two adjacent carbon atoms; in the latter case, they are, in particular, —[$CH_2$]$_3$— or —[$CH_2$]$_4$—.

The explanation given above applies analogously to homologs or to their derived radicals.

If $Q^1$ is a cycloalkyl group with n=5, $R^4$ and $R^5$ together with the adjacent carbon atoms to which they are attached preferably do not form a cyclohexane system.

If none of the symbols A, B, D and E is nitrogen, Y is a ($C_1$–$C_4$)-alkanediyl group and $Q^1$ is a cycloalkyl group of the formula II, with the exception of those cases in which $R^5$ is hydrogen and $R^4$ and Y are in the cis configuration relative to each other, then $R^4$ is preferably as defined above, with the exception of halogen, ($C_1$–$C_{10}$)-alkyl, ($C_1$–$C_4$)-haloalkoxy, phenoxy, phenyl and benzyloxy.

If at least one of the symbols A, B, D and E is nitrogen and $Q^1$ is a cycloalkyl group of the formula II, with the exception of those cases in which $R^5$ is hydrogen and $R^4$ and Y are in the cis configuration relative to each other, then $R^4$ is preferably as defined above with the exception of halogen, ($C_1$–$C_4$)-alkyl, ($C_1$–$C_4$)-haloalkyl, ($C_1$–$C_4$)-alkoxy and ($C_1$–$C_4$)-haloalkoxy.

Preferred compounds of the formula I are those in which
$R^1$ and $R^2$ are hydrogen, chlorine, fluorine, methyl or trifluoromethyl,
X is oxygen or NH,
Y is a direct bond,
Q is a cyclopentane or cyclobutane ring which is substituted in the 3-position or a cyclohexane or cycloheptane ring which is substituted in the 4-position,
the heterocyclic ring system has the formulae Ia, Ic or Id, and one of the radicals represented by A, B, D and E is nitrogen.

Particularly preferred compounds of the formula I are those in which
$R^1$ and $R^2$ are hydrogen and $R^1$, in the case of the compounds of the formula Ia, can also be fluorine,
X is oxygen or NH,
Y is a direct bond,
Q is a cyclohexane ring which is substituted in the 4-position,
the heterocyclic ring system has the formula Ia or Ic, in which A is nitrogen and B, D and E are in each case $CR^1$ or in which E is nitrogen and A, B and D in each case are $CR^1$, or Id, in which E is nitrogen and A, B and D are in each case $CR^1$, or A is nitrogen and B, D and E are in each case $CR^1$.

Other particularly preferred compounds of the formula I are those in which
$R^1$ is hydrogen or fluorine in the 8-position of a compound of the formula Ia,
$R^2$ is hydrogen,
X is oxygen or NH,
Y is a direct bond,
Q is a cyclohexane ring which is substituted in the 4-position and in which Y and $R^4$ are preferably in the cis configuration and these substituents are identical or different and are ($C_3$–$C_8$)-alkyl, ($C_5$–$C_8$)-cycloalkyl, ($C_1$–$C_8$)-alkoxy, cyclohexyloxy, cyclohexyl-($C_1$–$C_4$)-alkyl or phenyl and the phenyl radical can be unsubstituted or provided with one or two substituents and these substituents are identical or different and are in each case ($C_1$–$C_8$)-alkyl, cyclopentyl, cyclohexyl, trifluoromethyl, halogen, ($C_1$–$C_4$)-dialkylamino, ($C_1$–$C_4$)-alkylthio, ($C_1$–$C_8$)-alkoxy or ($C_1$–$C_4$)-alkoxy-($C_1$–$C_4$)-alkoxy or Q is an octahydroindanyl radical,
the heterocyclic ring system has the formula Ia or Ic where A is nitrogen and B, D and E are in each case $CR^1$, or Id where E is nitrogen and A, B and D are in each case $CR^1$, or where A is nitrogen and B, D and E are in each case CH.

Other particularly preferred compounds of the formula I are those in which $R^1$ can be hydrogen or, in the case of the compound of the formula Ia, also fluorine in the 8-position, $R^2$ is hydrogen, X is oxygen or NH, Y is a direct bond, Q is a cyclohexane ring which is monosubstituted in the 4-position and preferably in the cis configuration and this substituent is $(C_3-C_8)$-alkyl, $(C_5-C_8)$-cycloalkyl, $(C_1-C_8)$-alkoxy, cyclohexyloxy, cyclohexyl-$(C_1-C_4)$-alkyl or phenyl and the phenyl radical can be unsubstituted or provided with one substituent and this substituent can be $(C_1-C_4)$-alkyl, cyclopentyl, cyclohexyl, fluorine, chlorine or $(C_1-C_8)$-alkoxy, and the heterocyclic ring system has preferably the formula Ia.

The invention furthermore relates to a process for the preparation of compounds of the formula I which comprises reacting a compound of the formula IV

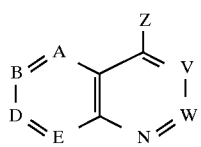

IV in which $R^1$, $R^2$, A, B, D, E, V and W are as defined under formula I and Z is a leaving group, such as halogen, alkylthio, alkanesulfonyloxy, arylsulfonyloxy, alkylsulfonyl or arylsulfonyl, with a nucleophile of the formula V

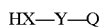 (V)

in which

X, Y and Q are as defined under formula I, and, if appropriate, converting the resulting compound into a salt thereof.

The above-described substitution reaction is known in principle. The leaving group Z can be varied within wide limits and can be, for example, a halogen atom, such as fluorine, chlorine, bromine or iodine, or alkylthio, such as methyl- or ethylthio, or alkanesulfonyloxy such as methane-, trifluoromethane- or ethanesulfonyloxy, or arylsulfonyloxy, such as benzenesulfonyloxy or toluenesulfonyloxy, or alkylsulfonyl, such as methyl- or ethylsulfonyl, or arylsulfonyl, such as phenyl- or toluenesulfonyl.

The abovementioned reaction is carried out in a temperature range from 20° to 150° C., expediently in the presence of a base and, if appropriate, in an inert organic solvent, such as N,N-dimethylformamide, N, N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

In the event that X is oxygen, then examples of suitable bases are carbonates, hydrogen carbonates, amides or hydrides of alkali metals or alkaline earth metals, such as sodium carbonate, sodium hydrogen carbonate, potassium carbonate, sodium amide or sodium hydride, and, in the event that X is NH, examples of suitable bases are carbonates, hydrogen carbonates, hydroxides, amides or hydrides of alkali metals or alkaline earth metals, such as sodium carbonate, sodium hydrogen carbonate, potassium carbonate, sodium hydroxide, sodium amide or sodium hydride, or organic bases, such as triethylamine or pyridine. A second equivalent of an amine V can also be used as an auxiliary base.

The starting compounds of the formula IV are either known, or they can be prepared analogously to known processes; see, for example:
quinolines: Org. Synth., Coll. Vol. 3, 272 (1955)
cinnolines: J. Org. Chem. 11, 419 (1946)
1,5-naphthyridine: J. Amer. Chem. Soc. 68, 1317 (1946) and British Patent 1,147,760
1,6-naphthyridines: J. Chem. Soc. 1960, 1790
1,7-naphthyridines: J. Org. Chem. 19, 2008 (1954)
1,8-naphthyridines: Synthesis 1974, 809
pyridopyrimidines: EP-A-414,386
pteridines: J. Chem. Soc. 1951, 474

The nucleophiles of the formula V, which are required as starting materials, can, in the event that X is oxygen, be prepared by known processes, for example by reducing a carbonyl group with a suitable reducing agent, for example a complex metal hydride, or, in the case of an aldehyde or ketone, also using hydrogen and a hydrogenation catalyst. To synthesize cyclohexanol derivatives, it is also possible to react suitable substituted phenols with hydrogen in the presence of a hydrogenation catalyst.

The nucleophiles of the formula V, which are required as starting materials, can, in the event that X is NH, be prepared by known processes, for example by reducing an oxime or nitrile with a suitable reducing agent, for example a complex metal hydride or hydrogen in the presence of an hydrogenation catalyst, reductive amination or Leuckart-Wallach reaction of an aldehyde or ketone or Gabriel reaction of an alkyl halide or alkyl tosylate. To synthesize cyclohexylamine derivatives, it is also possible to react suitable substituted anilines with hydrogen in the presence of a hydrogenation catalyst.

The active substances are well tolerated by plants and show a favourable toxicity to warm-blooded species while being suitable for controlling animal pests, in particular insects, arachnids, helminths and molluscs, very particularly preferably for controlling insects and arachnids, which are found in agriculture, livestock breeding, forests, in the protection of stored products and material and in the hygiene sector. They are active against normally sensitive and resistant species and against all or individual development stages. The abovementioned pests include:

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp., Eutetranychus spp.*

From the order of the Isopoda, for example, *Oniscus assellus, Armadium vulgar* and *Porcellio scaber.*

From the order of the Diplopoda, for example, *Blaniulus guttulatus.*

From the order of the Chilopoda, for example, *Geophilus carpophagus* and *Scutigera spp.*

From the order of the Symphyla, for example, *Scutigerella immaculata.*

From the order of the Thysanura, for example, *Lepisma saccharina.*

From the order of the Collembola, for example, *Onychiurus armatus*.

From the order of the Orthoptera, for example, *Blatta orientalis, Periplaneta americana, Leucophaea maderae, Blatella germanica, Acheta domesticus, Gryllotalpa spp., Locusta migratoria migratorioides, Melanoplus differentialis* and *Schistocerca gregaria*.

From the order of the Isoptera, for example, *Reticulitermes spp.*

From the order of the Anoplura, for example, *Phylloera vastatrix, Pemphigus spp., Pediculus humanus corporis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci*.

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonumus spp., Sitophilus spp., Otiorrhynchus sulcatus, Cosmopolites sordidus, Ceuthorrynchus assimilis, Hypera postica, Dermestes spp., Trogoderma, Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica*.

From the order of Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa*.

From the order of the Siphonaptera, for example, *Xenopsylla cheopis* and *Ceratophyllus spp.*

From the order of the Arachnida, for example, *Scorpio maurus* and *Latrodectus mactans*.

From the class of the Helminthes, for example, Haemonchus, Trichostrongulus, Ostertagia, Cooperia, Chabertia, Strongyloides, Oesophagostomum, Hyostrongulus, Ancylostoma, Ascaris and Heterakis and Fasciola, as well as plant-damaging nematodes, for example those of the genera Meloidogyne, Heterodera, Ditylenchus, Aphelenchoides, Radopholus, Globodera, Pratylenchus, Longidorus and Xiphinema.

From the class of the Gastropoda, for example, *Deroceras spp., Arion spp., Lymnaea spp., Galba spp., Succinea spp., Biomphalaria spp., Bulinus spp., Oncomelania spp.*

From the class of the Bivalva, for example, *Dreissena spp.*

The invention also relates to compositions, in particular to insecticidal and acaricidal compositions, which contain the compounds of the formula I in addition to suitable formulation auxiliaries.

The compositions according to the invention contain the active substances of the formula I in general in amounts of 1 to 95% by weight.

They can be formulated in a variety of ways, as predetermined by the biological and/or chemical-physical parameters. The following possibilities are therefore suitable for formulation: wettable powders (WP), emulsifiable concentrates (EC), aqueous solutions (SL), emulsions, sprayable solutions, dispersions on an oil or water base (SC), suspo emulsions (SE), dusts (DP), dressing compositions, granules in the form of microgranules, spray granules, coated granules and adsorption granules, water-dispersible granules (WG), ULV formulations, microcapsules, waxes or baits.

These individual types of formulation are known in principle and are described, for example, in: Winnacker-Küchler, "Chemische Technologie", [Chemical Technology], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1967; Winnacker-Küchler, "Chemische Technologie" [Chemical Technology], Volume 7, C. Hauser Verlag Munich, 4th Ed. 1986.

Combinations with other pesticidally active substances, fertilizers and/or growth regulators may also be prepared on the basis of these formulations, for example in the form of a readymix or a tank mix. Wettable powders are preparations which are uniformly dispersable in water and which, in addition to the active substance, also contain wetting agents, for example polyethoxylated alkylphenols, polyethoxylated fatty alcohols, alkylsulfonates or alkylphenolsulfonates, and dispersing agents, for example sodium ligninsulfonates, sodium 2,2'-dinaphthylmethane-6,6'-disulfonate, in addition to a diluent or inert substance.

Emulsifiable concentrates are prepared by dissolving the active substance in an organic solvent, for example butanol, cyclohexanone, dimethylformamide, xylene or else higher-boiling aromatic compounds or hydrocarbons, with the addition of one or more emulsifiers. Examples of emulsifiers which can be used are: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusts can be obtained by grinding the active substance with finely divided solid substances, for example talc, natural clays such as kaolin, bentonite or pyrophyllite, or diatomaceous earth. Granules can be produced either by spraying the active substance onto adsorptive, granulated inert material, or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

The concentration of active substance in wettable powders is, for example, about 10 to 90% by weight, the remainder to 100% by weight being composed of conventional formulation components. In the case of emulsifiable concentrates, the active substance concentration can be about 5 to 80% by weight. Formulations in the form of dusts usually contain 5 to 20% by weight of active substance, sprayable solutions about 2 to 20% by weight. In the case of granules, the active substance content depends partly on whether the active compound is liquid or solid and on which granulation auxiliaries, fillers and the like are used.

In addition, the abovementioned formulations of active substances contain, if appropriate, the adhesive and wetting agents, dispersants, emulsifiers, penetrants, solvents, fillers or carriers which are conventional in each case.

For use, the concentrates, in their commercially available form, are diluted, if appropriate, in a customary manner, for example using water in the case of wettable powders, emulsifiable concentrates, dispersions and, in some cases, also in the case of microgranules. Preparations in the form of dusts or granulated preparations and also sprayable solutions are usually not further diluted with other inert substances before use.

The application rate required varies with the external conditions, such as, inter alia, temperature and humidity. It can be varied within wide limits, for example between 0.0005 and 10.0 kg/ha or more of active ingredient, but it is preferably between 0.001 and 5 kg/ha.

The active substances according to the invention, in their commercially available formulations and in the use forms prepared with these formulations, can exist in the form of mixtures with other active substances, such as insecticides, attractants, sterilants, acaricides, nematicides, fungicides, growth regulators or herbicides.

Pesticides include, for example, phosphates, carbomates, carboxylates, formamidines, tin compounds, substances produced by microorganisms etc.

Preferred components for mixtures are
1. from the group comprising the phosphorus compounds acephate, azamethiphos, azinphos-ethyl, azinphosmethyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachloroethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemeton-methyl, parathion, parathionmethyl, phenthoate, phorate, phosalone, phosfolan, phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion;
2. from the group comprising the carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio(ethylideneamino)-N-methyl-N-(morpholinothio) carbamate (UC 51717);
3. from the group comprising the carboxylates allethrin, alphametrin, 5-benzyl-3-furylmethyl (E)-(1R)-cis-2,2-dimethyl-3-(2-oxothiolan-3-ylidenemethyl) cyclopropanecarboxylate, bioallethrin, bioallethrin ((S)-cyclopentyl isomer), bioresmethrin, biphenate, (RS)-1-cyano-1-(6-phenoxy-2-pyridyl)-methyl (1RS)-trans-3-(4-tert.butylphenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrins (natural products), resmethrin, tefluthrin, tetramethrin, tralomethrin;
4. from the group comprising the amidines amitraz, chlordimeform;
5. from the group comprising the tin compounds cyhexatin, fenbutatin oxide;
6. others abamectin, *Bacillus thuringiensis*, bensultap, binapacryl, bromopropylate, buprofezin, camphechlor, cartap, chlorbenzilate, chlorfluazuron, 2-(4-chlorophenyl)-4,5-diphenylthiophene (UBI-T 930), chlorfentezine, 2-naphthylmethyl cyclopropanecarboxylate (Ro 12-0470), cyromazin, ethyl N-(3,5-dichloro-4-(1,1,2,3,3,3-hexafluoro-1-propyloxy) phenyl) carbamoyl-2-chlorobenzocarboximidate, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2, 4-xylidine, dinobuton, dinocap, endosulfan, ethofenprox, (4-ethoxyphenyl)(dimethyl)(3-(3-phenoxyphenyl) propyl) silane, (4-ethoxyphenyl) (3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MT1 800), nuclear polyhedrosis and granulosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The active substance content of the use forms prepared from the commercially available formulations can be from 0.00000001 to 95% by weight of active substance, preferably between 0.00001 and 1% by weight.

Application is effected in a conventional fashion, matched to the use forms.

The active substances according to the invention are also suitable for controlling endo- and ectoparasites in the field of veterinary medicine or in the field of animal keeping.

The active substances according to the invention are applied here in a known fashion, such as by oral administration in the form of, for example, tablets, capsules, potions, granules, by dermal administration in the form of, for example, dipping, spraying, pouring-on and spotting-on and dusting, and also by parenteral administration in the form of, for example, an injection.

The novel compounds of the formula I according to the invention can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since excretion in the faeces occurs in an effective fashion, the development of insects in the animal faeces can be prevented very simply in this fashion. The dosages and formulations suitable in each case depend, in particular, on the type and stage of development of the productive animals and also on the degree of infestation, and can easily be determined and fixed by conventional methods. In the case of cattle, the novel compounds can be employed, for example, in dosages of 0.01 to 1 mg/kg of body weight.

The compounds of the formula I and their physiologically acceptable salts are also valuable pharmaceuticals. They have an antimicrobial, in particular an antimycotic, action and are suitable for preventing and treating fungal infections in humans and animals, in particular mammals.

The compounds of the formula I have a very good in vitro activity against dermatophytes, such as, for example, *Trichophyton mentagrophytes, Microsporum canis, Epidermophyton fluccosum*; against molds, such as, for example, *Aspergillus niger*, or against yeasts, such as, for example, *Candida albicans, C. tropicalis, Torulopsis glabrata* and *Trichosporon cutaneum*, or against Protozoa, such as *Trichomonas vaginalis* or *T. fetus*.

There is also a very good effect against various causative organisms of dermatomycoses (for example *Trichophyton mentagrophytes*) on guinea pigs after oral, parenteral or, in particular, local administration.

Fields of indication in human medicine which can be mentioned are, for example, dermatomycoses and systemic mycoses caused by *Trichophyton mentagrophytes* and other *Trichophyton species, Microsporon species, Epidermophyton floccosum*, yeasts and biphasic fungi, and molds.

Fields of indication in veterinary medicine which can be mentioned, for example, are all dermatomycoses and systemic mycoses, in particular those caused by the abovementioned causative organisms.

The present invention includes pharmaceutical preparations which contain, besides non-toxic, inert, pharmaceutically suitable excipients, one or more active substances according to the invention, or which are composed of one or more active substances according to the invention, and processes for making these preparations.

Non-toxic, inert, pharmaceutically suitable excipients are to be understood as meaning any type of solid, semisolid or liquid diluents, fillers and formulation auxiliaries.

Suitable dosage forms are, for example, tablets, coated tablets, capsules, pills, aqueous solutions, suspensions and emulsions, optionally sterile solutions for injection, non-aqueous emulsions, suspensions and solutions, ointments, creams, pastes, lotions, sprays and the like.

The abovementioned pharmaceutical preparations should preferably contain the therapeutically active compounds at a concentration of approximately 0.01 to 99.0, preferably approximately 0.05 to 50, % by weight of the total mixture.

The abovementioned pharmaceutical preparations can, in addition to the active substances according to the invention, also contain other pharmaceutical active substances.

The abovementioned pharmaceutical preparations are produced in the customary manner by known methods, for example by mixing of the active substance, or active substances, with the excipient, or excipients.

The present invention therefore also relates to the use of the active substances according to the invention and of pharmaceutical preparations which contain one or more active substances according to the invention in human and veterinary medicine for the prophylaxis and/or treatment of the abovementioned diseases.

The active substances or the pharmaceutical preparations can be administered locally, orally, parenterally, intraperitoneally and/or rectally.

In general, it has proved advantageous, both in human and in veterinary medicine, to administer the active substance, or active substances, according to the invention in total amounts of at least approximately 0.05, preferably 0.1, in particular 0.5, mg and not more than 200, preferably 100, in particular 30, mg/kg of body weight every 24 hours based on an adult of 75 kg body weight, if appropriate in the form of several individual doses, to achieve the desired results. The total amount is administered in 1 to 8, preferably in 1 to 3, single doses.

However, it may be necessary to deviate from the abovementioned dosage rates, namely as a function of the species and the body weight of the subject to be treated, the nature and severity of the disease, the type of preparation and administration of the pharmaceutical, and the period of time or interval within which it is administered. It may therefore suffice in some cases to use less than the abovementioned amount of active substance, while, in other cases, the abovementioned amount of active substance must be exceeded. The required optimal dosage rate and type of administration of the active substances can in each case easily be determined by any person skilled in the art on the basis of his expert knowledge.

The compounds of the formula I according to the invention are distinguished by an outstanding fungicidal activity. Fungal pathogens which have already penetrated the plant tissue can be controlled successfully in a curative manner. This is particularly important and advantageous in the case of those fungal diseases which can no longer be controlled effectively with the otherwise conventional fungicides once infection has taken place. The spectrum of action of the claimed compounds embraces a large number of a range of economically important phytopathogenic fungi, such as, for example, *Piricularia oryzae, Leptosphaeria nodorum, Drechslera teres*, powdery mildew species, *Venturia*

*inaequalis, Botrytis cinerea, Pseudocercosporella herpotrichoides*, and rusts, and also representatives of the Oomycetes, such as, for example, *Phytophthora infestans* and *Plasmopara viticola*.

The invention therefore also relates to a method of controlling phytopathogenic fungi which comprises applying a fungicidally active amount of a compound of the formula I or of a composition containing them to the phytopathogenic fungi or to the plants, areas or substrates which are infected by them or seeds; and also seed which has been treated or dressed in this manner.

In addition, the compounds according to the invention are also suitable for use in industrial fields, for example as wood preservatives, preservatives in paints, in cooling lubricants for metalworking or as preservative in drilling and cutting oils.

The active substances according to the invention can be used, in their commercially available formulations, either on their own or in combination with other fungicides known from the literature.

Examples of fungicides which are known from the literature and which can be combined according to the invention with the compounds of the formula I are the following products: aldimorph, andoprim (PM213), anilazine, BAS 480F, benalaxyl, benodanil, benomyl, binapacryl, bitertanol, bromuconazole, buthiobate, captafol, captan, carbendazim, carboxin, CGA 173506, chlorbenzthiazone, chlorthalonil, cymoxanil, cyproconazole, cyprofuram, dichlofluanid, dichlormezin, diclobutrazole, diethofencarb, difenconazole (CGA 169374), difluconazole, dimethirimol, dimethomorph, diniconazole, dinocap, dithianon, dodemorph, dodine, edifenfos, ethirimol, etridiazole, fenarimol, fenfuram, fenpiclonil, fenpropidin, fenpropimorph, fentin acetate, fentin hydroxide, fluazinam, fluobenzimine, flucuinconazole, fluorimide, flusilazole, flutolanil, flutriafol, folpet, fosetylaluminum, fuberidazole, fulsulfamide, furalaxyl, furconazol (LS 840606), furmecyclox, guazatine, hexaconazole, imazalil, imibenconazole, iprobenfos, iprodione, isoprothiolane, copper compounds such as copper oxychloride, oxine-copper, copper oxide, maneb, mancozeb, mepanipyrim, metconazole, mepronil, metalaxyl, methasulfocarb, methfuroxam, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RF7592, sulfur, tebuconazole, thiabendazole, thicyofen, thiofanate-methyl, thiram, tolclofos-methyl, tolylfluanid, triadimefon, triadimenol, tricyclazole, tridemorph, triflumizol, triforine, validamycin, vinchlozolin, zineb, sodium dodecylsulfonate, sodium dodecyl sulfate, sodium C13/C15-alcohol ether sulfonate, sodium cetostearyl phosphate ester, dioctyl sodium sulfosuccinate, sodium ispropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quarternized fatty amines, alkyldimethylbenzylammonium chloride and 1-hydroxyethyl-2-alkylimidazolin.

The abovementioned substances which can be used in the combinations are known active substances, most of which are described in Ch.R Worthing, U.S.B. Walker, The Pesticide Manual, 7th Edition (1983), British Crop Protection Council.

The active substance content of the use forms prepared with the commercially available formulations can vary within wide limits, and the active substance concentration of the use form can be between 0.0001 to 95% by weight % of active substance, preferably between 0.001 to 1% by weight.

They are used in one of the customary manners adapted to suit the use forms.

The examples which follow are intended to illustrate the invention, but not by way of limitation.

A. Formulation Examples a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium ligninsulfonate and 1 part by weight of sodium oleoylmethyltaurinate as wetting and dispersing agent, and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium ligninsulfonate and 51 parts by weight of water and grinding the mixture in a frictional ball mill to a fineness of below 5 microns.

d) An emulsifiable concentrate can be prepared from 15 parts by weight of active substance, 75 parts by weight of cyclohexanone as solvent and 10 parts by weight of ethoxylated nonylphenol (10 EO) as emulsifier.

e) Granules can be prepared from 2 to 15 parts by weight of active substance and an inert granule carrier material such as attapulgite, granulated pumice and/or quartz sand. It is expedient to use a suspension of the wettable powder of Example b) with a solids content of 30%, which is sprayed onto the surface of attapulgite granules, and these are dried and mixed intimately. The amount of the wettable powder is approximately 5% by weight and that of the inert carrier material approximately 95% of the finished granules.

B. Biological examples

Use as a fungicide

Example 1: *Botrytis cinerea*

Broad beans cv. "Herz Freya" or "Frank's Ackerperle" approximately 14 days old, were treated to runoff point with aqueous suspensions of the compounds according to the invention. After the spray coating had dried off, the plants were inoculated with a spore suspension (1.5 million spores/ml) of *Botrytis cinerea*. The plants were grown on in a controlled-environment cabinet at 20°–22° C. under relative atmospheric humidity of approximately 99%. The infection of the plants shows in the formation of black lesions on leaves and stalks. The experiments were evaluated approximately 1 week after inoculation. The disease level of the plants was scored in percent relative to untreated, 100% infected control plants.

The following compounds suppress disease completely when used at 500 mg of active substance/l spray mixture: Examples Nos. 3, 7, 19, 23, 25, 26, 45 and 80.

Example 2: *Plasmopara viticola*

Approximately 6 weeks after sowing, grapevine seedlings "Riesling/Ehrenfelder" were treated to runoff point using aqueous suspensions of the compounds according to the invention. After the spray coating had dried on, the plants were inoculated with a zoosporangia suspension of Plasmopara viticola and the dripping wet plants were placed for 4 to 5 hours into a controlled-environment cabinet at 23° C. at a relative atmospheric humidity of 80–90%.

After an incubation time of 7 days in the greenhouse, the plants were returned overnight into the controlled-environment cabinet to stimulate sporulation of the fungus. The disease was then evaluated. The disease level was expressed in % of diseased leaf area in comparison with the untreated, 100% infected control plants.

The following substances suppress disease completely when used at 500 mg of active substance/l spray mixture: Examples Nos. 3, 7, 19, 25, 26, 130 and 232.

Example 3: *Phytophthora infestans*

Tomato plants cv. "Rheinlands Ruhm" in the 3- to 4-leaf stage were wetted uniformly to runoff point using aqueous suspensions of the compounds according to the invention. After the plants had dried, they were inoculated with a zoosporangia suspension of Phytophthora infestans and kept for 2 days in a controlled-environment cabinet under ideal infection conditions. The plants were then grown on in the greenhouse until the symptoms were visible. The disease level was scored approximately 1 week after inoculation. The disease level of the plants was expressed in % of diseased leaf area in comparison with the untreated, 100% infected control plants.

The following substances suppress disease completely when used at 500 mg of active substance/l spray mixture: Example No. 45

Example 4: *Leptosphaeria nodorum*

Wheat plants cv. "Jubilar" in the 2-leaf stage were wetted to runoff point using aqueous suspensions of the preparations according to the invention. After the spray coating had dried on, the plants were inoculated with a Pyknospore suspension of *Leptosphaeria nodorum* and incubated for several hours in a controlled-environment cabinet at a relative atmospheric humidity of 100%. The plants were grown on in the greenhouse at a relative atmospheric humidity of approximately 90% until the symptoms became visible. The disease level was determined in % of diseased leaf area in comparison with the untreated, 100% infected control plants.

The following substances suppress disease completely when used at 500 mg of active substance/l spray mixture: Example No. 130

Example 5: *Erysiphe graminis*

Barley plants in the 3-leaf stage were inoculated with large amounts of conidia of powdery mildew of barley (Erysiphe graminis f. sp. hordei) and placed in a greenhouse at 20° C. and a relative atmospheric humidity of 90 to 95%. 24 hours after the inoculation, the plants were wetted uniformly with the abovementioned compounds. After an incubation time of 10 days, the plants were examined for the occurrence of powdery mildew of barley. The disease level was determined in % of diseased leaf area based on untreated, 100% infected control plants.

The following substances suppress disease completely when used at 500 mg of active substance/l spray mixture: Example No. 139

Example 6: *Pyrenophora teres*

Barley plants cv. "Igri" in the 2-leaf stage were wetted to runoff point with an aqueous suspension of the compounds according to the invention. After the spray coating had dried on, the plants were inoculated with an aqueous spore suspension of Pyrenophora teres and incubated for 16 hours in a controlled-environment cabinet at a relative atmospheric humidity of 100%. The infected plants were subsequently grown on in the greenhouse at 25° C. at a relative atmospheric humidity of 80%. The disease level was evaluated approximately 1 week after inoculation. The disease level was determined in % of diseased leaf area in comparison with untreated, 100% infected control plants.

The following substances suppress disease completely when used at 500 mg of active substance/l spray mixture: Example No. 139.

Use as an insecticide and acaricide

Example 7

Broad beans (*Vicia faba*) which were heavily populated with black bean aphid (*Aphis fabae*) are sprayed up to the stage at which run-off began using aqueous dilutions of concentrates of wettable powders, active substance content 250 ppm. The mortality of the aphids is determined after 3 days. A 100% mortality can be achieved with the compounds of Examples Nos. 4, 5, 10, 20, 27, 28, 130 and 139.

Example 8

Paper filter disks onto which eggs of the large milkweed bug (*Oncopeltus fasciatus*) have been placed are treated with in each case 0.5 ml of aqueous dilution of the test formulation. After the coating has dried on, the Petri dish is sealed, and the inside is kept at maximum atmospheric humidity. After the dishes have been kept at room temperature, the ovicidal activity was determined after 7 days. A mortality of 100% was achieved with the compounds of Example Nos. 3, 10, 19, 23, 27, 45, 130, 139, 208, 215 and 280 at an active substance content of 250 ppm.

Example 9

Bean plants which were heavily populated with whitefly (*Trialeurodes vaporariorum*) were sprayed to the beginning of the run-off point using aqueous suspensions of concentrates of wettable powders (250 ppm active substance content). After the plants had been placed in the greenhouse, they were subjected to microscope checks after 14 days, resulting in a 100% mortality in the case of each preparation containing the active substances of Example Nos. 4, 5, 10, 19, 20, 24, 27, 28, 130 and 139.

Example 10

Active substances which were dissolved in acetone were applied orally to butterfly larvae (L4) of tobacco hornworm (*Manduca sexta*). After active substance of Example No. 3 or 8 ($2 \times 10^{-4}$ g of a.i./animal) had been applied, a mortality of 100% was found after 48 hours.

Example 11

Freshly deposited eggs of *Diabrotica undecimpunctata* (southern corn rootworm) were sprayed, on paper filters, with in each case 2 ml of an aqueous suspension of wettable powders (active substance content 250 ppm) and were subsequently observed at room temperature. After 5 days, the eggs were examined for mortality.

The preparations of Example Nos. 3, 4, 27, 130, 139 and 232 showed a 100% activity against eggs of *Diabrotica undecimpunctata*.

Example 12

*Spodoptera littoralis* (Egyptian cotton leafworm) larvae in the $L_3$ stage were introduced into Petri dishes filled with nutrient medium, and these dishes together with the larvae were sprayed with 2 ml of an aqueous suspension of wettable powder containing 250 ppm (Corresponding to 6000 l of water/ha). After the spray coating had dried on, the Petri dishes were sealed and stored for 5 days at 21° C. After 5 days, the compound of Example No. 28 had caused a mortality of the Spodoptera larvae of 100%.

Example 13

Bean plants (*Phaseolus v.*) which were heavily infested with the two-spotted spider mite (*Tetranychus urticae*, full population) were sprayed with the aqueous dilution of a concentrate of wettable powder, containing 250 ppm of the active substance in question. The mortality of the mites was checked after 7 days. A mortality rate of 100% was achieved with the compounds of Examples Nos. 4, 10, 19, 20, 23, 24, 27, 130, 133 and 139.

Use as antiparasitic agent

Example 14

In vitro test on tropical cattle ticks (*Boophilus microplus*)

The following experimental set-up allowed the effectiveness of the compounds according to the invention against ticks to be confirmed.

To produce a suitable preparation of active substance, the active substances were dissolved to 10% strength (w/v) in a mixture composed of dimethylformamide (85 g), nonylphenolpolyglycol ether (3 g) and ethoxylated castor oil (7 g), and the resulting emulsion concentrates were diluted with water to a test concentration of 500 ppm.

Batches of ten females of the tropical tick *Boophilus microplus* which had sucked themselves full were immersed for five minutes in these active substance dilutions. The ticks were subsequently dried on paper filters and then attached, with their backs, to an adhesive film-in order to deposit eggs. The ticks were kept in an incubator at 28° C. at an atmospheric humidity of 90%.

As a control, the female ticks were immersed just in water. Two weeks after the treatment, the inhibition of oviposition was used to determine the effectiveness. 100% means that no ticks have deposited eggs, 0 that all ticks have deposited eggs.

In this test, a 100% inhibition of oviposition is caused, in each case, by the compounds 14, 20, 27 and 28 at an active substance concentration of 500 ppm.

Use as antimycotic agent

Example 15

The test for antimycotic activity was carried out in a serial dilution test on dermatophytes (*Trichophyton mentagrophytes, Trichophyton rubrum, Microsporum canis*), yeasts (*Candida albicans*) and molds (*Aspergillus niger*) (Materials and Methods: Microtitration Technology, published in Mykosen 27, 14 (1984). As can be seen from the table below, the compounds according to the invention show good antimycotic properties against these fungi in in vitro tests.

TABLE

| | Minimum inhibitory concentration μg/l | | | | |
|---|---|---|---|---|---|
| Preparation Comp. No. | Trichophyton mentagrophytes (100/25) | Trichophyton rubrum (101/58) | Microsporum canis (150/353) | Candida albicans (200/175) | Aspergillus niger (500/284) |
| 27 | 7.81 | 0.97 | 0.06 | 7.81 | 7.81 |
| 23 | 1.95 | 1.95 | 1.95 | 3.50 | 15.63 |

C. Preparation Examples

Example 1:

4-(4-Phenylcyclohexylamino)quinoline

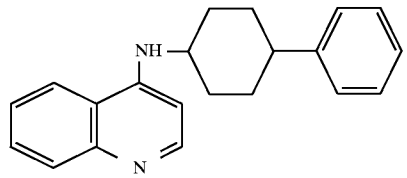

3.3 g (20 mmol) of 4-chloroquinoline and 8.8 g (50 mmol) of 4-phenylcyclohexylamine (Cis/trans isomer mixture obtained from 4-phenylcyclohexanone by reductive amination) were stirred for 8 hours at 200° C. without solvent. The mixture was taken up in water/dichloroethane, and the organic phase was dried and concentrated. The crude product was chromatographed on silica gel using ethyl acetate/methanol 19:1. The trans-cyclohexylamino derivative was eluted first (400 mg of colorless oil which solidified slowly). After a mixed fraction, 400 mg of the cis isomer (oil, solidified slowly) were finally obtained.

NMR (CDCl$_3$) cis form 5.20 d NH; 4.97 m (narrow) NHCH; trans form 4.98 d NH; 3.60 m (broad) NHCH Example 2:

4-(cis-4-tert-Amylcyclohexyloxy)quinoline

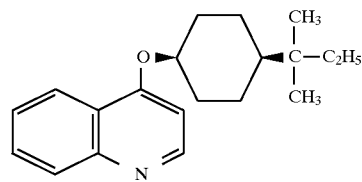

0.60 g of sodium hydride (80% strength) (20 mmol) was introduced into 25 ml of dimethylformamide. After 3.4 g (20 mmol) of cis-4-tert-amylcyclohexanol (obtained from 4-tert-amylcyclohexanone by reduction with L-Selectride®) had been added, the mixture was stirred at 70° C. until the evolution of hydrogen had ceased. After the mixture had been cooled to room temperature, 3.3 g (20 mmol) of 4-chloroquinoline were added, and the mixture was heated for 5 hours at 90° C. After the solvent had been stripped off, the residue was taken up in water/dichloroethane, and the organic phase was washed twice with water, dried and concentrated. The crude product was chromatographed on silica gel using ethyl acetate. 2.0 g of yellow oil were obtained.

$^1$H NMR 4.80 (m) OCH

Example 3:

4-(4-Cyclohexylcyclohexyloxy)quinoline

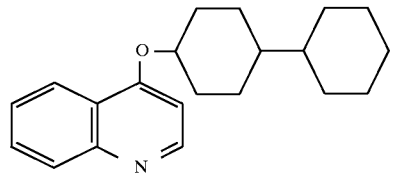

Analogously to Example 2, 0.75 g (25 mmol) of sodium hydride (80% strength), 3.65 g (20 mmol) of 4-cyclohexylcyclohexanol (obtained by catalytic hydrogenation of 4-cyclohexylphenol (50° C., 150 bar, Rh/C) and 3.27 g (20 mmol) of 4-chloroquinoline were reacted. After chromatography on silica gel using ethyl acetate as eluent, 0.33 g of trans isomer (colorless oil), solidified slowly, m.p. 145° to 146° C.) was initially obtained and then, after a mixture fraction, 0.41 g of cis isomer (colorless oil, solidified slowly, m.p. 94° to 96° C.).

$^1$H NMR (CDCl$_3$) trans form: 4.35 m (broad) OCH; cis form: 4.8 m (narrow) OCH Preparation Examples
Abbreviations used in the tabulated examples:
T¹ 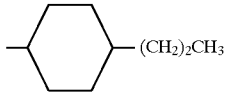
T² 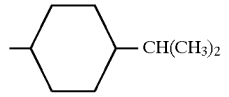
T³ 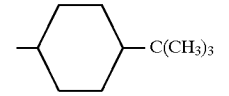
T⁴ 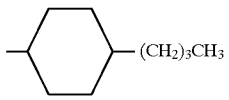
T⁵ 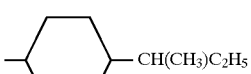
T⁶ 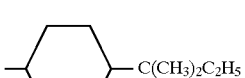
T⁷ 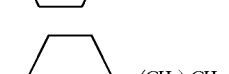
T⁸ 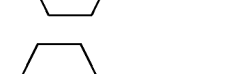
T⁹ 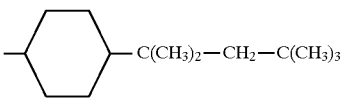
T¹⁰ 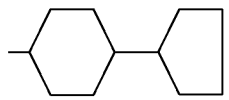
T¹¹ 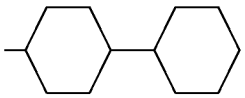
T¹² 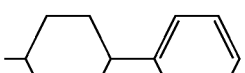
T¹³ 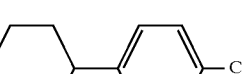
T¹⁴ 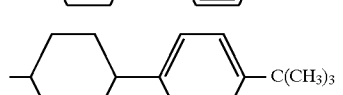
T¹⁵ 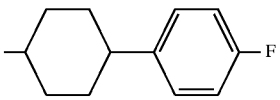
T¹⁶ 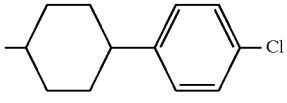
T¹⁷ 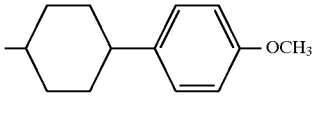
T¹⁸ 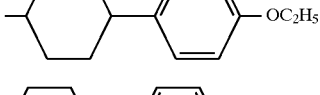
T¹⁹ 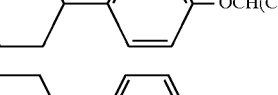
T²⁰ 
T²¹ 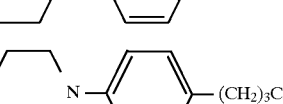
T²² 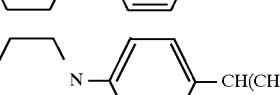
T²³ 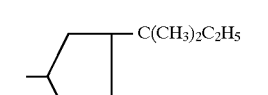
T²⁴ 
T²⁵ 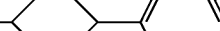
T²⁶ 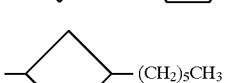
T²⁷ 
T²⁸ 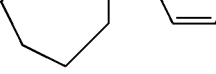

T²⁹ 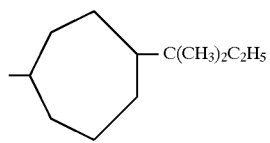

T³⁰ 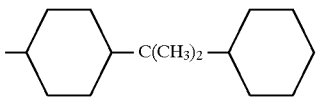

T³¹ 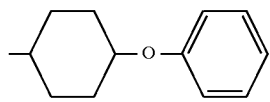

T³² 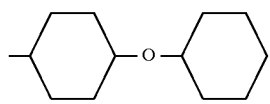

T³³ 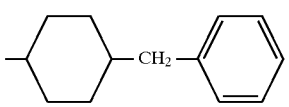

T³⁴ 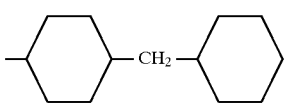

T³⁵ 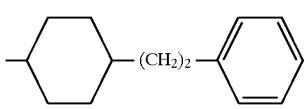

T³⁶ 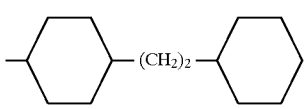

T³⁷ 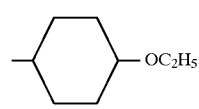

T³⁸ 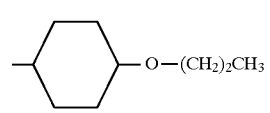

T³⁹ 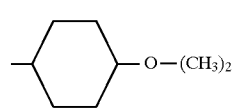

T⁴⁰ 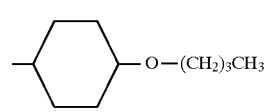

T⁴¹ 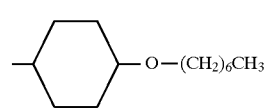

T⁴² 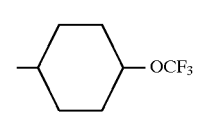

T⁴³ 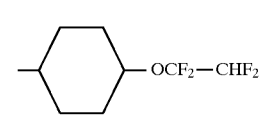

T⁴⁴ 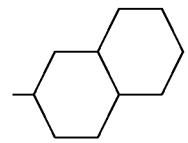

T⁴⁵ 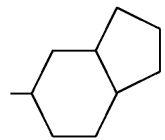

T⁴⁶ 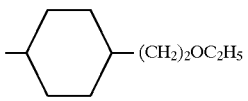

The compounds of the table below are prepared analogously to the procedure described in Examples 1 or 2.

a) quinolines

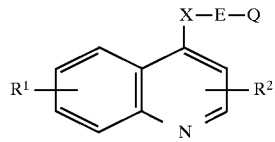

| Comp. No. | $R^1$ | $R^2$ | X | E | Q | Isomerism of the cycloalkane | m.p. [°C.] |
|---|---|---|---|---|---|---|---|
| 1 | H | H | NH | — | $T^1$ | cis | |
| 2 | H | H | NH | — | $T^2$ | cis | |
| 3 | H | H | NH | — | $T^3$ | mixture | oil |
| 4 | H | H | O | — | $T^3$ | mixture | 86–87 |
| 5 | 8-F | H | NH | — | $T^3$ | cis | oil |
| 6 | 8-F | H | O | — | $T^3$ | cis | |
| 7 | 7-Cl | H | NH | — | $T^3$ | cis | oil |
| 8 | 7-CF₃ | H | NH | — | $T^3$ | cis | oil |
| 9 | H | H | NH | — | $T^4$ | cis | |
| 10 | H | H | O | — | $T^4$ | cis | oil |
| 11 | H | H | NH | — | $T^5$ | cis | oil |
| 12 | H | H | O | — | $T^5$ | cis | oil |
| 13 | H | H | NH | — | $T^6$ | cis | |
| 14 | H | H | O | — | $T^6$ | cis | oil |
| 15 | H | H | NH | — | $T^7$ | cis | |
| 16 | H | H | O | — | $T^7$ | cis | |
| 17 | H | H | NH | — | $T^8$ | cis | |
| 18 | H | H | O | — | $T^8$ | cis | |
| 19 | H | H | NH | — | $T^9$ | mixture | resin |
| 20 | H | H | O | — | $T^9$ | cis | oil |
| 21 | H | H | NH | — | $T^{10}$ | cis | |
| 22 | H | H | O | — | $T^{10}$ | cis | 51–53 |
| 23 | H | H | NH | — | $T^{11}$ | mixture | resin |
| 24 | H | H | O | — | $T^{11}$ | cis | 94–96 |
| 25 | H | H | NH | — | $T^{12}$ | cis | |
| 26 | H | H | NH | — | $T^{12}$ | trans | |
| 27 | H | H | O | — | $T^{12}$ | cis | 99–100 |
| 28 | 8-F | H | NH | — | $T^{12}$ | cis | 176–178 |
| 29 | 8-F | H | O | — | $T^{12}$ | cis | |
| 30 | H | 2-CH₃ | NH | — | $T^{12}$ | mixture | resin |
| 31 | H | H | NH | — | $T^{13}$ | cis | |
| 32 | H | H | O | — | $T^{13}$ | cis | |
| 33 | H | H | NH | — | $T^{14}$ | cis | |
| 34 | H | H | O | — | $T^{14}$ | cis | |
| 35 | H | H | NH | — | $T^{15}$ | cis | |
| 36 | H | H | O | — | $T^{15}$ | cis | |
| 37 | H | H | NH | — | $T^{16}$ | cis | |
| 38 | H | H | O | — | $T^{16}$ | cis | |
| 39 | H | H | NH | CHCH₃ | $T^{16}$ | mixture | oil |

-continued

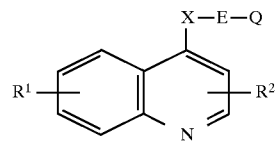

| Comp. No. | R¹ | R² | X | E | Q | Isomerism of the cycloalkane | m.p. [°C.] |
|---|---|---|---|---|---|---|---|
| 40 | H | H | O | CHCH₃ | $T^{16}$ | mixture | oil |
| 41 | H | H | NH | — | $T^{17}$ | cis | |
| 42 | H | H | O | — | $T^{17}$ | cis | |
| 43 | H | H | NH | — | $T^{17}$ | cis | |
| 44 | H | H | O | — | $T^{17}$ | cis | |
| 45 | H | H | NH | — | $T^{18}$ | cis | |
| 46 | H | H | O | — | $T^{18}$ | cis | oil |
| 47 | H | H | NH | — | $T^{19}$ | cis | |
| 48 | H | H | O | — | $T^{19}$ | cis | oil |
| 49 | H | H | NH | — | $T^{20}$ | cis | |
| 50 | H | H | O | — | $T^{20}$ | cis | 139–140 |
| 51 | H | H | NH | — | $T^{21}$ | cis | |
| 52 | H | H | O | — | $T^{21}$ | cis | |
| 53 | H | H | NH | — | $T^{22}$ | — | 144–145 |
| 54 | H | H | O | — | $T^{22}$ | — | |
| 55 | H | H | NH | — | $T^{23}$ | — | |
| 56 | H | H | O | — | $T^{23}$ | — | |
| 57 | H | H | NH | — | $T^{24}$ | mixture | oil |
| 58 | H | H | O | — | $T^{24}$ | cis | |
| 50 | H | H | NH | — | $T^{25}$ | cis | |
| 60 | H | H | O | — | $T^{25}$ | cis | |
| 61 | H | H | NH | — | $T^{26}$ | cis | |
| 62 | H | H | O | — | $T^{26}$ | cis | |
| 63 | H | H | NH | — | $T^{27}$ | mixture | |
| 64 | H | H | O | — | $T^{27}$ | cis | |
| 65 | H | H | NH | — | $T^{28}$ | mixture | |
| 66 | H | H | O | — | $T^{28}$ | cis | |
| 67 | H | H | NH | — | $T^{29}$ | mixture | |
| 68 | H | H | O | — | $T^{29}$ | cis | |
| 69 | H | H | NH | — | $T^{30}$ | cis | |
| 70 | H | H | O | — | $T^{30}$ | cis | |
| 71 | H | H | NH | — | $T^{31}$ | cis | |
| 72 | H | H | O | — | $T^{31}$ | cis | |
| 73 | H | H | NH | — | $T^{32}$ | cis | |
| 74 | H | H | O | — | $T^{32}$ | cis | |
| 75 | H | H | NH | — | $T^{33}$ | cis | |
| 76 | H | H | O | — | $T^{34}$ | cis | |
| 77 | H | H | NH | — | $T^{35}$ | cis | |
| 78 | H | H | O | — | $T^{35}$ | cis | |
| 79 | H | H | NH | — | $T^{36}$ | cis | |
| 80 | H | 2-CH₃ | NH | — | $T^{9}$ | cis | oil |
| 100 | H | H | O | — | $T^{36}$ | cis | |
| 101 | H | H | NH | — | $T^{37}$ | cis | |
| 102 | H | H | O | — | $T^{37}$ | cis | |
| 103 | H | H | NH | — | $T^{38}$ | cis | |
| 104 | H | H | O | — | $T^{38}$ | cis | |
| 105 | H | H | NH | — | $T^{39}$ | cis | |
| 106 | H | H | O | — | $T^{39}$ | cis | |
| 107 | H | H | NH | — | $T^{40}$ | cis | |
| 108 | H | H | O | — | $T^{40}$ | cis | |
| 109 | H | H | NH | — | $T^{41}$ | cis | |
| 110 | H | H | O | — | $T^{41}$ | cis | |
| 111 | H | H | NH | — | $T^{42}$ | cis | |
| 112 | H | H | O | — | $T^{42}$ | cis | |
| 113 | H | H | NH | — | $T^{43}$ | cis | |
| 114 | H | H | O | — | $T^{43}$ | cis | |
| 115 | H | H | NH | — | $T^{44}$ | mixture | |
| 116 | H | H | O | — | $T^{44}$ | cis | |
| 117 | H | H | NH | — | $T^{45}$ | cis | |
| 118 | H | H | O | — | $T^{45}$ | cis | |
| 119 | H | H | NH | — | $T^{46}$ | cis | |
| 120 | H | H | O | — | $T^{46}$ | cis | | b) 1,5-naphthyridines

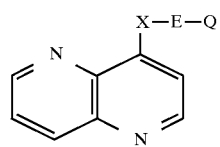

| Comp. No. | X | E | Q | Isomerism of the cycloalkane | m.p. [°C.] |
|---|---|---|---|---|---|
| 120 | NH | — | $T^{1}$ | cis | |
| 121 | O | — | $T^{1}$ | cis | |
| 122 | NH | — | $T^{2}$ | cis | |
| 123 | O | — | $T^{2}$ | cis | |
| 124 | NH | — | $T^{3}$ | cis | |
| 125 | O | — | $T^{3}$ | cis | |
| 126 | NH | — | $T^{4}$ | cis | |
| 127 | O | — | $T^{4}$ | cis | |
| 128 | NH | — | $T^{5}$ | cis | |
| 129 | O | — | $T^{5}$ | cis | |
| 130 | NH | — | $T^{6}$ | cis | oil |
| 131 | O | — | $T^{6}$ | cis | |
| 132 | NH | — | $T^{9}$ | cis | |
| 133 | O | — | $T^{9}$ | cis | oil |
| 134 | NH | — | $T^{10}$ | cis | |
| 135 | O | — | $T^{10}$ | cis | |
| 136 | NH | — | $T^{11}$ | cis | |
| 137 | O | — | $T^{11}$ | cis | |
| 138 | NH | — | $T^{12}$ | cis | |
| 139 | O | — | $T^{12}$ | cis | 111–112 |
| 140 | NH | CHCH₃ | $T^{16}$ | mixture | |
| 141 | NH | — | $T^{18}$ | cis | |
| 142 | O | — | $T^{18}$ | cis | |
| 143 | NH | — | $T^{19}$ | cis | |
| 144 | O | — | $T^{19}$ | cis | | c) 1,6-naphthyridines

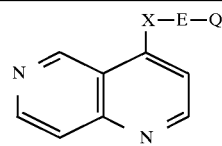

| Comp. No. | X | E | Q | Isomerism of the cycloalkane | m.p. [°C.] |
|---|---|---|---|---|---|
| 150 | NH | — | $T^{1}$ | cis | |
| 151 | O | — | $T^{1}$ | cis | |
| 152 | NH | — | $T^{2}$ | cis | |
| 153 | O | — | $T^{2}$ | cis | |
| 154 | NH | — | $T^{4}$ | cis | |
| 155 | O | — | $T^{4}$ | cis | |
| 156 | NH | — | $T^{9}$ | cis | |
| 157 | O | — | $T^{9}$ | cis | oil |
| 158 | NH | — | $T^{11}$ | cis | |
| 159 | O | — | $T^{11}$ | cis | |
| 160 | NH | — | $T^{12}$ | cis | |
| 161 | O | — | $T^{12}$ | cis | 137–138 |
| 162 | NH | — | $T^{18}$ | cis | 155–156 |
| 163 | O | — | $T^{18}$ | cis | |
| 164 | NH | — | $T^{19}$ | cis | |
| 165 | O | — | $T^{19}$ | cis | | d) 1,7-naphthyridines

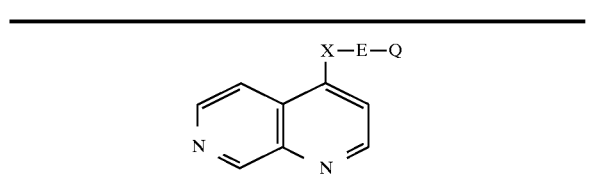

| Comp. No. | X | E | Q | Isomerism of the cycloalkane | m.p. [°C.] |
|---|---|---|---|---|---|
| 170 | NH | — | $T^1$ | cis | |
| 171 | O | — | $T^1$ | cis | |
| 172 | NH | — | $T^2$ | cis | |
| 173 | O | — | $T^2$ | cis | |
| 174 | NH | — | $T^4$ | cis | |
| 175 | O | — | $T^4$ | cis | |
| 176 | NH | — | $T^9$ | cis | |
| 177 | O | — | $T^9$ | cis | |
| 178 | NH | — | $T^{11}$ | cis | |
| 179 | O | — | $T^{11}$ | cis | |
| 180 | NH | — | $T^{12}$ | cis | |
| 181 | O | — | $T^{12}$ | cis | |
| 182 | NH | — | $T^{18}$ | cis | |
| 183 | O | — | $T^{18}$ | cis | |
| 184 | NH | — | $T^{19}$ | cis | |
| 185 | O | — | $T^{19}$ | cis | | e) 1,8-naphthyridines

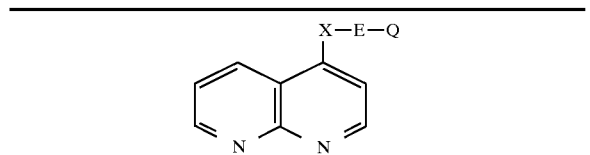

| Comp. No. | X | E | Q | Isomerism of the cycloalkane | m.p. [°C.] |
|---|---|---|---|---|---|
| 190 | NH | — | $T^1$ | cis | |
| 191 | O | — | $T^1$ | cis | |
| 192 | NH | — | $T^2$ | cis | |
| 193 | O | — | $T^2$ | cis | |
| 194 | NH | — | $T^3$ | cis | |
| 195 | O | — | $T^3$ | cis | |
| 196 | NH | — | $T^4$ | cis | |
| 197 | O | — | $T^4$ | cis | |
| 198 | NH | — | $T^5$ | cis | |
| 199 | O | — | $T^5$ | cis | |
| 200 | NH | — | $T^6$ | cis | |
| 201 | O | — | $T^6$ | cis | |
| 202 | NH | — | $T^9$ | cis | |
| 203 | O | — | $T^9$ | cis | |
| 204 | NH | — | $T^{10}$ | cis | |
| 205 | O | — | $T^{10}$ | cis | |
| 206 | NH | — | $T^{11}$ | cis | |
| 207 | O | — | $T^{11}$ | cis | |
| 208 | NH | — | $T^{12}$ | cis | |
| 209 | O | — | $T^{12}$ | cis | |
| 210 | NH | $CHCH_3$ | $T^{16}$ | mixture | |
| 211 | NH | — | $T^{18}$ | cis | |
| 212 | O | — | $T^{18}$ | cis | |
| 213 | NH | — | $T^{19}$ | cis | |
| 214 | O | — | $T^{19}$ | cis | |

Compound No. 215

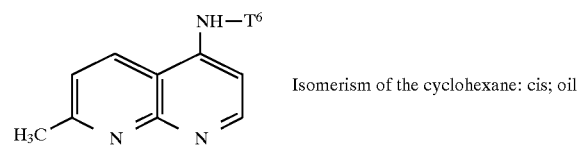

Isomerism of the cyclohexane: cis; oil f) Pyrido[3,2-d]pyrimidines

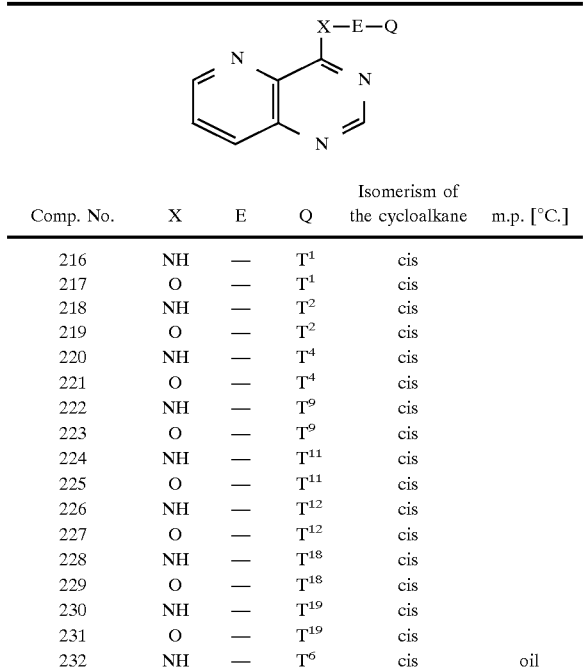

| Comp. No. | X | E | Q | Isomerism of the cycloalkane | m.p. [°C.] |
|---|---|---|---|---|---|
| 216 | NH | — | $T^1$ | cis | |
| 217 | O | — | $T^1$ | cis | |
| 218 | NH | — | $T^2$ | cis | |
| 219 | O | — | $T^2$ | cis | |
| 220 | NH | — | $T^4$ | cis | |
| 221 | O | — | $T^4$ | cis | |
| 222 | NH | — | $T^9$ | cis | |
| 223 | O | — | $T^9$ | cis | |
| 224 | NH | — | $T^{11}$ | cis | |
| 225 | O | — | $T^{11}$ | cis | |
| 226 | NH | — | $T^{12}$ | cis | |
| 227 | O | — | $T^{12}$ | cis | |
| 228 | NH | — | $T^{18}$ | cis | |
| 229 | O | — | $T^{18}$ | cis | |
| 230 | NH | — | $T^{19}$ | cis | |
| 231 | O | — | $T^{19}$ | cis | |
| 232 | NH | — | $T^6$ | cis | oil | g) Pyrido[4,3-d]pyrimidines

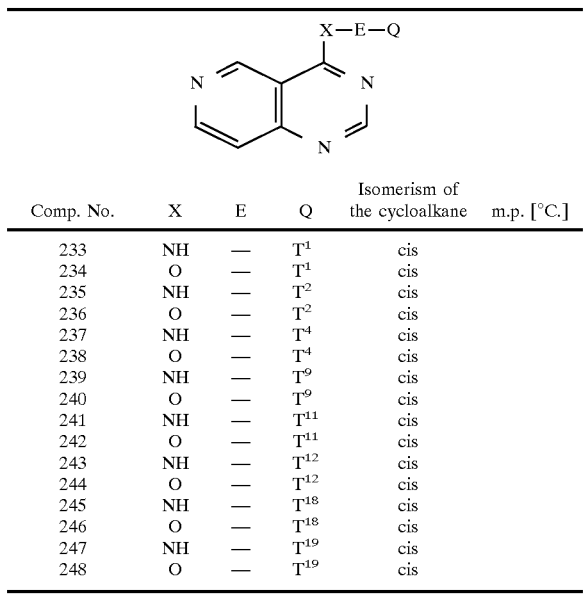

| Comp. No. | X | E | Q | Isomerism of the cycloalkane | m.p. [°C.] |
|---|---|---|---|---|---|
| 233 | NH | — | $T^1$ | cis | |
| 234 | O | — | $T^1$ | cis | |
| 235 | NH | — | $T^2$ | cis | |
| 236 | O | — | $T^2$ | cis | |
| 237 | NH | — | $T^4$ | cis | |
| 238 | O | — | $T^4$ | cis | |
| 239 | NH | — | $T^9$ | cis | |
| 240 | O | — | $T^9$ | cis | |
| 241 | NH | — | $T^{11}$ | cis | |
| 242 | O | — | $T^{11}$ | cis | |
| 243 | NH | — | $T^{12}$ | cis | |
| 244 | O | — | $T^{12}$ | cis | |
| 245 | NH | — | $T^{18}$ | cis | |
| 246 | O | — | $T^{18}$ | cis | |
| 247 | NH | — | $T^{19}$ | cis | |
| 248 | O | — | $T^{19}$ | cis | | h) Pyrido[3,4-d]pyrimidines

[Structure with X—E—Q substituent on pyrido[3,4-d]pyrimidine]

| Comp. No. | X | E | Q | Isomerism of the cycloalkane | m.p. [°C.] |
|---|---|---|---|---|---|
| 250 | NH | — | $T^1$ | cis | |
| 251 | O | — | $T^1$ | cis | |
| 252 | NH | — | $T^2$ | cis | |
| 253 | O | — | $T^2$ | cis | |
| 254 | NH | — | $T^4$ | cis | |
| 255 | O | — | $T^4$ | cis | |
| 256 | NH | — | $T^9$ | cis | |
| 257 | O | — | $T^9$ | cis | |
| 258 | NH | — | $T^{11}$ | cis | |
| 259 | O | — | $T^{11}$ | cis | |
| 260 | NH | — | $T^{12}$ | cis | |
| 261 | O | — | $T^{12}$ | cis | |
| 262 | NH | — | $T^{18}$ | cis | |
| 263 | O | — | $T^{18}$ | cis | |
| 264 | NH | — | $T^{19}$ | cis | |
| 265 | O | — | $T^{19}$ | cis | | i) Pyrido[2,3-d]pyrimidines

[Structure with X—E—Q substituent on pyrido[2,3-d]pyrimidine]

| Comp. No. | X | E | Q | Isomerism of the cycloalkane | m.p. [°C.] |
|---|---|---|---|---|---|
| 270 | NH | — | $T^1$ | cis | |
| 271 | O | — | $T^1$ | cis | |
| 272 | NH | — | $T^2$ | cis | |
| 273 | O | — | $T^2$ | cis | |
| 274 | NH | — | $T^4$ | cis | |
| 275 | O | — | $T^4$ | cis | |
| 276 | NH | — | $T^9$ | cis | |
| 277 | O | — | $T^9$ | cis | oil |
| 278 | NH | — | $T^{11}$ | cis | |
| 279 | O | — | $T^{11}$ | cis | |
| 280 | NH | — | $T^{12}$ | cis | 213–214 |
| 281 | O | — | $T^{12}$ | cis | |
| 282 | NH | — | $T^{18}$ | cis | |
| 283 | O | — | $T^{18}$ | cis | |
| 284 | NH | — | $T^{19}$ | cis | |
| 285 | O | — | $T^{19}$ | cis | | j) Pteridines

[Structure with X—E—Q substituent on pteridine]

| Comp. No. | X | E | Q | Isomerism of the cycloalkane | m.p. [°C.] |
|---|---|---|---|---|---|
| 290 | NH | — | $T^1$ | cis | |
| 291 | O | — | $T^1$ | cis | |
| 292 | NH | — | $T^2$ | cis | |
| 293 | O | — | $T^2$ | cis | |
| 294 | NH | — | $T^4$ | cis | |
| 295 | O | — | $T^4$ | cis | |
| 296 | NH | — | $T^9$ | cis | |
| 297 | O | — | $T^9$ | cis | |
| 298 | NH | — | $T^{11}$ | cis | |
| 299 | O | — | $T^{11}$ | cis | |
| 300 | NH | — | $T^{12}$ | cis | |
| 301 | O | — | $T^{12}$ | cis | |
| 302 | NH | — | $T^{18}$ | cis | |
| 303 | O | — | $T^{18}$ | cis | |
| 304 | NH | — | $T^{19}$ | cis | |
| 305 | O | — | $T^{19}$ | cis | | k) Cinnolines

[Structure with X—E—Q substituent on cinnoline]

| Comp. No. | X | E | Q | Isomerism of the cycloalkane | m.p. [°C.] |
|---|---|---|---|---|---|
| 310 | NH | — | $T^1$ | cis | |
| 311 | O | — | $T^1$ | cis | |
| 312 | NH | — | $T^2$ | cis | |
| 313 | O | — | $T^2$ | cis | |
| 314 | NH | — | $T^4$ | cis | |
| 315 | O | — | $T^4$ | cis | |
| 316 | NH | — | $T^9$ | cis | |
| 317 | O | — | $T^9$ | cis | |
| 318 | NH | — | $T^{11}$ | cis | |
| 319 | O | — | $T^{11}$ | cis | |
| 320 | NH | — | $T^{12}$ | cis | |
| 321 | O | — | $T^{12}$ | cis | |
| 322 | NH | — | $T^{18}$ | cis | |
| 323 | O | — | $T^{18}$ | cis | |
| 324 | NH | — | $T^{19}$ | cis | |
| 325 | O | — | $T^{19}$ | cis | |

We claim:

1. A compound of the formula I

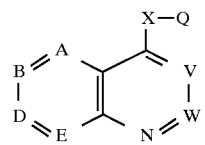

in which
two of the symbols A, B, D and E are in each case $CR^1$ and
the remaining two symbols are in each case CH, or
one of the remaining two symbols is CH and the other is nitrogen, and
one of the symbols V and W is $CR^2$ and the other is CH, the symbol V being exclusively CH or $CR^2$ in the case where none of the symbols A, B, D and E is nitrogen,
$R^1$ radicals are identical or different and are hydrogen, halogen, $(C_1-C_4)$-alkyl, $(C_1-C_4)$-alkoxy, halo-$(C_1-C_4)$-alkyl, or halo-$(C_1-C_4)$-alkoxy, $R^2$ is hydrogen, halogen, $(C_1-C_4)$-alkyl, $(C_1-C_4)$-alkoxy, halo-$(C_1-C_4)$-alkyl, or halo-$(C_1-C_4)$-alkoxy, X is NR, oxygen, sulfur, SO or $SO_2$, R is hydrogen or $(C_1-C_4)$-alkyl, Q is a cycloalkyl group of the formula II

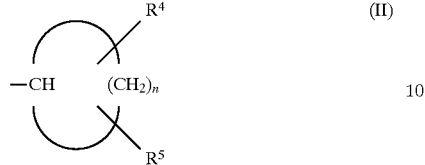

in which n is an integer from 3 to 7, $R^4$ is $(C_1-C_{12})$-alkyl, $(C_3-C_8)$-cycloalkyl, $(C3-C_8)$-cycloalkyl-$(C_1-C_4)$-alkyl, $(C_1-C_8)$-alkoxy, $(C_3-C_8)$-cycloalkoxy, $(C_1-C_4)$-alkoxy-$(C_1-C_4)$-alkyl, $(C_3-C_8)$-cycloalkyl-$(C_1-C_4)$-alkoxy, $(C_1-C_8)$-alkoxycarbonyl, $(C_1-C_4)$-alkoxy-$(C_1-C_4)$-alkoxycarbonyl, $(C_3-C_8)$-cycloalkoxycarbonyl, $(C_1-C_8)$-alkylcarbamoyl, di-$(C_1-C_8)$-alkylcarbamoyl, N-piperidinocarbonyl, N-morpholinocarbonyl, $(C_3-C_8)$-cycloalkylcarbamoyl, $(C_1-C_8)$-alkylcarbonyloxy, $(C_3-C_8)$-cycloalkylcarbonyloxy, $(C_1-C_8)$-alkylcarbonylamino, $(C_3-C_8)$-cycloalkylcarbonylamino, tri-$(C_1-C_8)$-alkylsilyl, di-$(C_1-C_8)$-alkyl-$(C_1-C_8)$-cycloalkylsilyl, di-$(C_1-C_8)$-alkyl(phenyl-$(C_1-C_4)$-alkyl)silyl, di-$(C_1-C_8)$-alkyl-$(C_1-C_4)$-haloalkylsilyl, $(C_1-C_4)$-haloalkyl, halogen, $(C_1-C_4)$-haloalkoxy, $(C_1-C_4)$-haloalkoxycarbonyl, $(C_1-C_4)$-haloalkylcarbamoyl, $(C_3-C_8)$-haloalkylcarbonyloxy, $(C_3-C_8)$-haloalkylcarbonylamino, optionally substituted heteroaryl, optionally substituted phenyl, optionally substituted naphthyl, optionally substituted biphenylyl, optionally substituted phenyl-$(C_1-C_4)$-alkyl, optionally substituted benzyloxy, optionally substituted benzyloxy-$(C_1-C_4)$-alkyl, optionally substituted benzylthio, optionally substituted phenoxycarbonyl, optionally substituted benzyloxycarbonyl, optionally substituted phenylcarbamoyl, optionally substituted benzylcarbamoyl, optionally substituted benzoyloxy, optionally substituted phenylacetyloxy, optionally substituted benzoylamino, optionally substituted phenylacetylamino, optionally substituted phenylthio or optionally substituted phenoxy, wherein the heteroaryl group is thienyl, furyl, benzofuryl, pyrrolyl, imidazolyl, pyrazolyl, pyridyl, pyrazinyl, pyrimidinyl, pyridazinyl, oxazolyl, isoxazoly, thiazolyl, isothiazolyl and tetrazolyl and when substituted are substituted with one or two substituents, and these substituents are identical or different and are selected from the group consisting of $(C_1-C_8)$-alkyl, $(C_3-C_8)$-cycloalkyl, $(C_1-C_4)$-haloalkyl, halogen, $(C_1-C_4)$-dialkylamino, $(C_1-C_4)$-alkylthio, $(C_1-C_8)$-alkoxy, $(C_1-C_4)$-haloalkoxy, $(C_1-C_4)$-alkoxy-$(C_1-C_4)$-alkoxy, $H_5C_2$—O—$[CH_2$—$CH_2$—O—$]_x$ where x=2, 3 or 4, 2-(tetrahydro-2H-pyran-2-yloxy)-ethoxy, $(C_2-C_8)$-alkenyl, $(C_2-C_8)$-alkynyl, benzyloxy, which itself optionally has one or two identical or different substituents selected from the groups consisting of $(C_1-C_4)$-alkyl, $(C_1-C_4)$-haloalkyl, $(C_1-C_4)$-alkoxy, $(C_1-C_4)$-haloalkoxy and halogen in the phenyl radical, or tri-$(C_1-C_4)$-alkylsilylmethoxy, $(C_3-C_8)$-cycloalkyl-$(C_1-C_4)$-alkoxy, 1,3-dioxolane-2-ylmethoxy, tetrahydrofur-2-ylmethoxy or tetrahydro-2H-pyran-2-ylmethoxy, $R^5$ is hydrogen or has one of the meanings of $R^4$, $R^4$ being in the 3-position if n=3 or 4, otherwise in the 4-position of the cycloalkyl group of formula II, and $R^4$ being in the cis-position relative to X, and wherein when $R^4$ and $R^5$, identical or different, are either $(C_1-C_8)$-alkyl or $(C_1-C_8)$-alkoxy, optionally one hydrogen atom in two adjacent substituents in $R^4$ and $R^5$ is replaced by a joint C—C bond which links these two substituents, $R^4$ and $R^5$, if not already embraced by the above definitions, together are $(C_1-C_6)$-alkanediyl which is bonded to identical or different carbon atoms, in which one or two $CH_2$ groups is optionally replaced by oxygen or sulfur and one or two ethanediyl groups is optionally replaced by ethenediyl groups.

2. A compound of the formula I

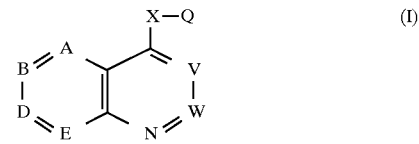

in which $R^1$, $R^2$, A, B, D, E, V, W, and X are as defined in claim 1 and Q is a cycloalkyl group of the formula II

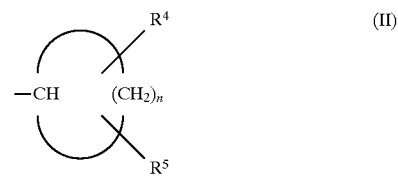

n is an integer from 3 to 6

$R^4$ and $R^5$ are identical or different and are in each hydrogen, $(C_1-C_{12})$-alkyl, $(C_3-C_8)$-cycloalkyl, $(C_3-C_8)$-cycloalkyl-$(C_1-C_4)$-alkyl $(C_1-C_8)$-alkoxy, $(C_3-C8)$-cycloalkoxy, $(C_1-C_4)$-alkoxy-$(C_1-C_4)$-alkyl, $(C_3-C_8)$-cycloalkyl-$(C_1-C_4)$-alkoxy, $(C_1-C_8)$-alkoxycarbonyl, $(C_3-C_8)$-cycloalkoxycarbonyl, $(C_1-C_8)$-alkylcarbamoyl, di-$(C_1-C_8)$-alkylcarbamoyl, N-piperidinocarbonyl, N-morpholino-carbonyl, $(C_3-C_8)$cycloalkylcarbamoyl, $(C_1-C_8)$-alkylcarbonyloxy, $(C_3-C_8)$-cycloalkylcarbonyloxy, $(C_1-C_8)$-alkylcarbonylamino, $(C_3-C_8)$-cycloalkylcarbonylamino, tri-$(C_1-C_8)$-alkylsilyl, di-$(C_1-C_8)$-alkyl-$(C_3-C_8)$-cycloalkylsilyl, di-$(C_1-C_8)$-alkyl-(phenyl$(C_1-C_4)$-alkyl)silyl, di$(C_1-C_8)$-alkyl $(C_1-C_4)$haloalkylsilyl, $(C_1-C_4)$-haloalkyl, halogen, $(C_1-C_4)$-haloalkylcarbamoyl, $(C_3-C_8)$-haloalkylcarbonyloxy, $(C_3-C_8)$-haloalkylcarbonylamino, optionally substituted heteroaryl, optionally substituted phenyl, optionally substituted naphthyl, optionally substituted biphenylyl, optionally substituted phenyl-$(C_1-C_4)$-alkyl, optionally substituted benzyloxy, optionally substituted benzyloxy-$(C_1-C_4)$alkyl, optionally substituted benzylthio, optionally substituted phenoxycarbonyl, optionally substituted benzyloxycarbonyl, optionally substituted phenylcarbamoyl, optionally substituted benzylcarbamoyl, optionally substituted benzoyloxy, optionally substituted phenylacetyloxy, optionally substituted benzoylamino, optionally substituted phenylacetylamino, optionally substituted phenylthio or optionally substituted phenoxy, wherein the heteroaryl group is thienyl, furyl, benzofuryl, pyrrolyl, imidazolyl, pyrazolyl, pyridyl, pyrazinyl, pyrimidinyl, pyridazinyl, oxazolyl, isoxazolyl, thiazolyl, isothiazolyl and tetrazolyl and when substituted are substituted with one or two substituents, and these substituents are identical or different and are selected from the group consisting of $(C_1-C_8)$-alkyl, $(C_3-C_8)$-cycloalkyl, $(C_1-C_4)$-haloalkyl, halogen, $(C_1-C_4)$-dialkylamino, $(C_1-C_4)$-alkylthio, $(C_1-C_8)$-alkoxy, $(C_1-C_4)$-dialkylamino, $(C_1-C_4)$-alkylthio, $(C_1-C_8)$-alkoxy-$(C_1-C_4)$-alkoxy, $H_5C_2-O-[CH_2-CH_2-O-]_x$ where x=2, 3 or 4, 2-(tetrahydro-2H-pyran-2-yloxy)-ethoxy, $(C_2-C_8)$-alkenyl, $(C_2-C_8)$-alkynyl, benzyloxy, which itself optionally has one or two identical or different substituents selected from the group consisting of$(C_1-C_4)$-alkyl, $(C_1-C_4)$-haloalkyl, $(C_1-C_4)$-alkoxy, $(C_1-C_4)$-haloalkoxy and halogen in the phenyl radical, or tri-$(C_1-C_4)$-alkylsilylmethoxy, $(C_3-C_8)$-cyclo-alkyl-$(C_1-C_4)$-alkoxy, 1,3-dioxolan-2-ylmethoxy, tetrahydrofur-2-ylmethoxy or tetrahydro-2H-pyran-2-ylmethoxy, and wherein, when $R^4$ and $R^5$, identical or different, are either $(C_1-C_8)$-alkyl or $(C_1-C_8)$-alkoxy optionally one hydrogen atom in two adjacent substituted in $R^4$ and $R^5$ is replaced by a joint C—C bond which links these two substituents with the proviso that at least one of the radicals $R^4$ and $R^5$ is other than hydrogen and at least one of these radicals $R^4$ and $R^5$ is in the cis configuration relative to X, or a salt thereof.

3. A compound of the formula I as claimed in claim 1 in which
$R^1$ and $R^2$ are hydrogen and $R^1$, in the case of the compounds of the formula Ia, can also be fluorine,
X is oxygen or NH,
Q is a cyclohexane ring which is cis substituted in the 4-position,
the heterocyclic ring system has the formula Ia or Ic, in which A is nitrogen and B, D and E are in each case $CR^1$ or in which E is nitrogen and A, B and D in each case are $CR^1$, or a salt thereof.

4. A compound according to claim 1 which has the formula

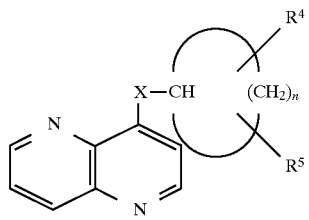

n is 5,
$R^4$ is in the 4-position and $R^4$ is cis-orientated relative to X and wherein $R^5$ is hydrogen.

5. A compound of the formula I as claimed in claim 1, in which
$R^1$ can be hydrogen or, in the case of the compound of the formula Ia, also fluorine in the 8-position,
$R^2$ is hydrogen,
X is oxygen or NH,
Q is a cyclohexane ring which is monosubstituted in the 4-position and this substituent is $(C_3-C_8)$-alkyl, $(C_5-C_8)$-cycloalkyl, $(C_1-C_8)$-alkoxy, cyclohexyloxy, cyclohexyl-$(C_1-C_4)$-alkyl or phenyl and the phenyl radical can be unsubstituted or provided with one substituent and this substituent can be $(C_1-C_4)$-alkyl, cyclopentyl, cyclohexyl, fluorine, chlorine or $(C_1-C_8)$-alkoxy, and the heterocyclic ring system is formula Ia, or a salt thereof.

6. A compound according to claim 1, which has the formula

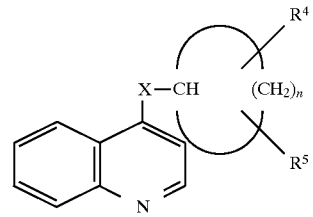

where
n is 5
$R^4$ is in the 4-position and $R^4$ is cis-orientated relative to X, and wherein
$R^5$ is hydrogen.

7. A compound of the formula I as claimed in claim 2, in which $R^5$ is hydrogen, or a salt thereof.

8. A compound of the formula I as claimed in claim 2, in which $R^4$ is in the (n+1)/2+1 position if n is an odd number and in the n/2+1 position of the cycloalkyl radical of the formula II if n is an even number, or a salt thereof.

9. A compound of the formula I as claimed in claim 2.

10. A compound of the formula I as claimed in claim 6, in which Q is a monocyclic radical $Q^1$ as defined in claim 1 and the remaining variables are as defined in claim 1 or a salt thereof.

11. A process for the preparation of a compound of the formula I as claimed in claim 1 which comprises reacting a compound of the formula IV

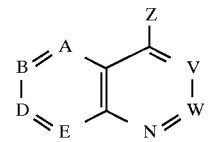

in which
$R^1$, $R^2$, A, B, D, E, V and W are as defined in claim 1 and Z is a leaving group, with a nucleophile of the formula V $$HX-Y-Q \qquad (V)$$

in which
X, Y and Q are as defined under formula I in claim 1, and, if appropriate, converting the resulting compound into a salt thereof.

12. A composition containing at least one compound as claimed in claim 1 and at least one formulation auxiliary.

13. A fungicidal composition as claimed in claim 12 containing a fungicidally effective amount of at least one compound as claimed in claim 1 together with the additives or auxiliaries conventionally used for this application.

14. An insecticidal, acaricidal or nematicidal composition as claimed in claim 12 containing at least one compound as claimed in claim 1 together with the additives or auxiliaries conventionally used for these applications.

15. A crop protection composition containing a fungicidally, insecticidally, acaricidally or nematicidally effective amount of at least one compound as claimed in claim 1 and at least one other active substance, preferably from amongst the series comprising the fungicides, insecticides, attractants, sterilants, acaricides, nematicides and herbicides, together with the auxiliaries and additives conventionally used for this application.

16. A composition for use in the protection of wood or as a preservative in paints, in cooling lubricants for metalworking or in drilling and cutting oils, containing an effective amount of at least one compound as claimed in claim 1 together with the auxiliaries and additives conventionally used for these applications.

17. A compound as claimed in claim 1 or compositions as claimed in claim 12 for use in the control of endo- or ectoparasites.

18. A process for the preparation of a composition as claimed in claim 1, which comprises combining the active substance and the other additives and bringing the mixture into a suitable use form.

19. A compound according to claim 1 wherein A is N; B, D and E are $CR^1$; and W and V are Ch.

20. A compound according to claim 1 wherein A, B, D and E are $CR^1$ and W and V are CH.

21. A method of controlling phytopathogenic fungi, which comprises applying to these fungi or to the plants, areas or substrates infested with them or to seed, a fungicidally effective amount of a compound as claimed in claim 1 or of a composition as claimed in claim 12.

22. A method of controlling insect pests, Acarina and nematodes, in which an effective amount of a compound as claimed in claim 1 or of a composition as claimed in claim 12 is applied to these insect pests, Acarina and nematodes or to the plants, areas or substrates infested with them.

23. A compound according to claim 1, which is selected from the group consisting of

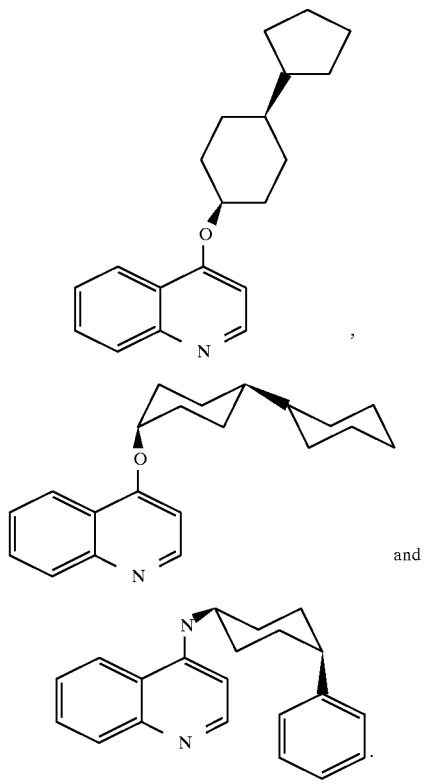

24. A pharmaceutical preparation containing an antimycotically effective amount of a compound as claimed in claim 1 and a physiologically acceptable excipient.

25. A compound as claimed in claim 1 or a composition as claimed in claim 24 for use as an antimycotic agent.

26. A method for the prophylaxis of mycoses, which comprises administering an amount of a compound as claimed in claim 1 which is prophylactically effective against mycoses.

27. A method for the treatment of mycoses, which comprises administering an effective amount of a compound as claimed in claim 1.

28. Seed, treated or dressed with a compound as claimed in claim 1 or with a composition as claimed in claim 12.

29. A compound of the formula I

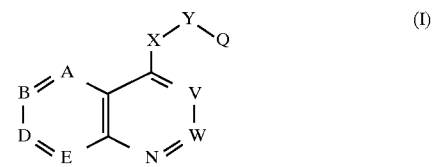

in which $R^1$, $R^2$, B, D, E, V and W are as defined in claim 1,

X is oxygen or NH,

Y is a direct bond, and

Q is a cycloalkyl group of the formula II

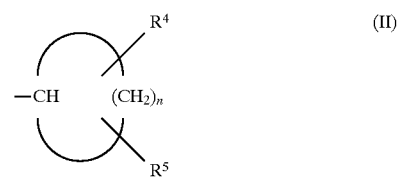

n is 5, $R^4$ is in the 4-position and $R^4$ is cis-oriented X, respectively, and wherein $R^5$ is hydrogen.

30. A compound according to claim 1, in which $R^1$ and $R^2$ are hydrogen, chlorine, fluorine, methyl and/or trifluoromethyl, X is oxygen or NH, Q is a cyclopentane or cyclobutane ring which is cis-substituted in the 3-position or a cyclohexane or cycloheptane ring which is cis-substituted in the 4-position, the heterocyclic ring system has the formulae Ia or Ic

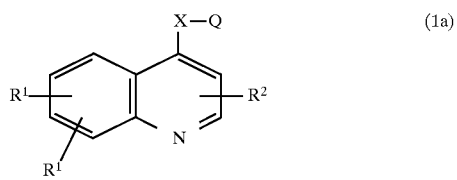

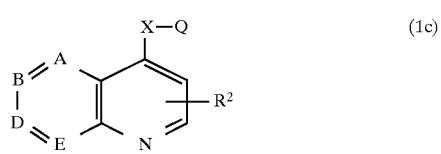

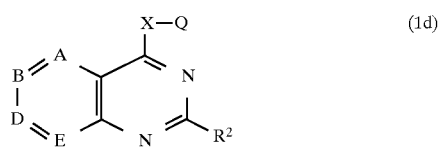

and one of the radicals represented by A, B, D and E is nitrogen, or a salt thereof.

31. A compound according to claim 1, in which

R¹ is hydrogen or fluorine in the 8-position of a compound of the formula Ia,

R² is hydrogen,

X is oxygen or NH,

Q is a cyclohexane ring which is cis-substituted in the 4-position and these substituents are identical or different and are $(C_3–C_8)$-alkyl, $(C_5–C_7)$-cycloalkyl, $(C_1–C_8)$alkoxy or phenyl wherein phenyl radical is unsubstituted or substituted with one or two substituents and these substituents are identical the different and are in each case $(C_1–C_8)$-alkyl, cyclopentyl, cyclohexyl, trifluoromethyl, halogen, $(C_1–C_4)$-dialkylamino, $(C_1–C_4)$-alkylthio, $(C_1–C_8)$-alkoxy or $(C_1–C_4)$-alkoxy-$(C_1–C_4)$alkoxy or Q is an octahydroindanyl radical, the heterocyclic ring system has the formula Ia or Ic where A is nitrogen and B, D and E are in each case CR¹ or a salt thereof.

32. A compound according to claim 4 which is

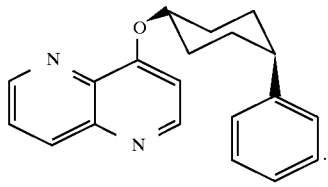

33. A method of combatting fungi which comprises applying an effective amount of a compound according to claim 1 to said fungi or to a habitat where they reside.

34. A method for preserving wood, paints, cooling lubricants for metal working or in drilling and cutting oils from fungi which comprise adding an effective amount of a compound according to claim 1 or a composition according to claim 12 to said wood, paints, cooling lubricants or drilling or cutting oils.

* * * * *